US010808232B2

(12) United States Patent
Yung et al.

(10) Patent No.: US 10,808,232 B2
(45) Date of Patent: Oct. 20, 2020

(54) DYNAMICALLY-ADAPTIVE LIVE THERAPEUTIC AGENTS AND METHODS OF USE THEREOF

(71) Applicant: Lawrence Livermore National Security, LLC, Livermore, CA (US)

(72) Inventors: Mimi-Cho Yung, Milpitas, CA (US); Matthew A. Coleman, Oakland, CA (US); Patrik D'haeseleer, Alameda, CA (US); Howard Harris, Los Angeles, CA (US); Yongqin Jiao, Pleasanton, CA (US); Kenneth W. Overton, San Jose, CA (US); Dan Mcfarland Park, Dublin, CA (US); Brent W. Segelke, San Ramon, CA (US); Sergio E. Wong, Tracy, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 26 days.

(21) Appl. No.: 15/438,638

(22) Filed: Feb. 21, 2017

(65) Prior Publication Data
US 2018/0236012 A1    Aug. 23, 2018

(51) Int. Cl.
| | | |
|---|---|---|
| A61K 35/74 | (2015.01) |
| C07K 14/33 | (2006.01) |
| C12Q 1/04 | (2006.01) |
| C07K 14/00 | (2006.01) |
| C12N 9/22 | (2006.01) |
| C12N 15/11 | (2006.01) |
| C07K 14/245 | (2006.01) |
| C07K 14/315 | (2006.01) |

(52) U.S. Cl.
CPC ............... *C12N 9/22* (2013.01); *C07K 14/00* (2013.01); *C07K 14/245* (2013.01); *C07K 14/315* (2013.01); *C07K 14/33* (2013.01); *C12N 15/11* (2013.01); *C12Q 1/04* (2013.01); *A61K 35/74* (2013.01); *C12N 2310/20* (2017.05)

(58) Field of Classification Search
CPC ........ G06N 3/002; H03M 1/361; H03M 1/74; C12N 15/63; C12N 15/635; C12N 11/00; C12N 11/14; C12N 15/70; C12N 17/06; C12N 17/14; C12N 2319/02; C12N 23/03; C12N 2319/034; C12N 2319/035; C12N 2710/24132; C12N 1/066; C12Q 1/005; C12Q 1/02; C12Q 10/25; C12Q 1/06; C12Q 1/6806; C12Q 1/66; C12Q 1/6804; C12Q 2531/113; C12Q 2565/629; C12Q 1/6825; C12Q 2525/205; C12Q 2527/109; C12Q 2537/125; C12Q 2563/116; C12Q 2563/143; C12Q 2565/634; G01N 2333/726; G01N 2800/102; G01N 2800/2821; G01N 2800/302; G01N 33/5023; G01N 33/5038; G01N 33/54353; G01N 33/566; G01N 33/569; G01N 33/56911; G01N 33/56916; G01N 33/5695; G01N 33/56961; G01N 33/74; G01N 2333/11; G01N 2333/31; G01N 2333/33; G01N 33/5308; G01N 33/56938; G01N 33/56983; A61K 38/1841; A61K 38/39; A61K 49/0013; A61K 49/0047; A61K 49/0097; A61K 49/1896; C07K 14/495; C07K 14/78; C07K 2319/55; C07K 2319/60; C07K 2319/61; B01L 2200/10; B01L 2300/0681; B01L 3/502707; B82Y 30/00; B82Y 40/00; C01B 2202/34; C01B 2202/36; C01B 32/15
See application file for complete search history.

(56) References Cited

PUBLICATIONS

Awad et al. Gut Microbes. 2014; 5: 579-593, 2014.*
Fagan et al. J. Biol. Chem. 286: 27483-27493, 2011.*
Ang, J., et al., "Tuning Response Curves for Synthetic Biology," ACS Synth Biol. Oct. 18, 2013; 2(10): 547-567.
Centers for Disease, Control and Prevention: https://www.cdc.gov/HAI/organisms/cdiff/Cdif—infect.html, accessed Oct. 23, 2018, 3pages.
Dawson, L., et al., "Clostridium difficile-a continually evolving and problematic pathogen," Infect Genet Evol. Dec. 2009;9(6):1410-7.
Eldar, A., et al., "Functional roles for noise in genetic circuits," Send to Nature. Sep. 9, 2010;467(7312):167-73.
Gupta, S., et al., "Genetically programmable pathogen sense and destroy," ACS Synth. Biol. 2013, 2 (12), pp. 715-723.
Moon, H., et al., "Developing genetically engineered encapsulin protein cage nanoparticles as a targeted delivery nanoplatform," Biomacromolecules, Oct. 13, 2014;15(10):3794-801.
Nagaro, K., et al., "NonToxigenic Clostridium difficile Protects Hamsters against Challenge with Historic and Epidemic Strains of Toxigenic BI/NAP1/027 C. difficile." Antimicrobial Agents and Chemotherapy, Nov. 2013;57(11):5266-70.
Paredes-Sabja, D., et al., "Clostridium difficile spore biology: sporulation, germination, and spore structural proteins," Trends Microbiol Jul. 2014; 22(7), pp. 406-416.
Saeidi, N., et al., "Engineering microbes to sense and eradicate Pseudomonas aeruginosa, a human pathogen," Molecular Systems Biology 7, Article 521, 2011, 11 paces.
Sorg, J., et al., "Bile salts and glycine as cogerminants for Clostridium difficile spores," Journal of Bacteriology, Apr. 2008;190(7):2505-2512.

* cited by examiner

*Primary Examiner* — Sarvamangala Devi
(74) *Attorney, Agent, or Firm* — Perkins Coie, LLP

(57) ABSTRACT

This disclosure provides microbes engineered to detect virulent and spore states of pathogens and release an appropriate therapeutic response accordingly and compositions and methods of use of the same.

10 Claims, 5 Drawing Sheets
Specification includes a Sequence Listing.

DYNAMICALLY-ADAPTIVE LIVE THERAPEUTIC AGENTS AND METHODS OF USE THEREOF

STATEMENT REGARDING FEDERALLY SPONSORED RESEARCH

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Current use, and the misuse or overuse, of broad spectrum antibiotics has significantly limited their effectiveness against pathogens, especially those pathogens that have life-cycles that can evade these drugs. As pathogens develop new resistance mechanisms, the ability to treat even common infectious diseases diminishes and results in higher medical expenses, prolonged illnesses, and even death.

*Clostridium difficile* (*C. difficile* or C. diff) bacterial infections cause diarrhea as well as more serious intestinal conditions such as colitis. *C. difficile* is a leading cause of intestinal infection and is common in people on prolonged antibiotic regimens, the elderly, and those in hospitals. *C. difficile* has proven difficult to treat, with recurrence resulting in more than 20% of patients. Recurrence is caused in part because *C. difficile* is naturally resistant to broad spectrum antibiotics due to formation of a dormant, spore state. Suppression of natural gut microbiota during antibiotic treatment further contributes to the spread and impact of *C. difficile*. In fact, *C. difficile* kills more than 14,000 people a year in the United States alone and adds approximately $4.8 billion in annual U.S. healthcare costs.

Novel approaches that can respond dynamically with the changing life cycle states of resistant pathogens are needed.

SUMMARY

Methods and materials are provided for detecting and responding to different pathogen states.

In some aspects the disclosure provides genetically engineered microbes comprising a dual pathogen state detection system, the dual pathogen detection system comprising: (a) a first sensor for detection of a virulent form of a pathogen, wherein the first sensor is operatively connected to a virulent secretion system; and (b) a second sensor for detection of a spore form of the pathogen, wherein the second sensor is operatively connected to a spore secretion system.

In some aspects the disclosure provides compositions comprising an amount of the genetically engineered microbe according to any embodiment disclosed and described herein.

In some aspects the disclosure provides methods of inhibiting a pathogenic microbe comprising delivering a genetically engineered microbe as in any embodiment disclosed and described herein to a composition comprising the pathogenic microbe.

In some aspects the disclosure provides methods of detecting a state of a pathogenic microbe comprising delivering the genetically engineered microbe as in any embodiment disclosed and described herein to a composition comprising the pathogenic microbe.

In some aspects the disclosure provides methods of treating or preventing a pathogenic infection in a subject in need thereof comprising administering to the subject an effective amount of a composition comprising genetically engineered microbes as in any embodiment disclosed and described herein.

In some embodiments, the microbe is a bacterium, for example, a Gram-positive bacterium. In some embodiments, the bacterium is *Escherichia coli Nissle* 1917 or *Lactococcus lactis* (*L. lactis*). In some embodiments, the microbe is a viable microbe.

In some embodiments, at least the first sensor or the second sensor detects a protein on the surface of the pathogen.

In some embodiments, the modified cell surface receptor comprises an antibody, antimicrobial peptide, or fragment thereof.

In some embodiments, the first sensor detects a toxin secreted by the virulent pathogen, for example, TcdA or TcdB.

In some embodiments, the second sensor detects a cell surface protein on the pathogen.

In some embodiments, the cell surface protein is a cell wall protein or a spore coat protein, for example, a BclA glycoprotein or a cysteine (CdeC)-rich protein.

In some embodiments, at least one of the first sensor or the second sensor does not detect a quorum sensing molecule.

In some embodiments, the virulent secretion system produces one or more agents in an encapsulated shell, one or more Clustered Regularly Interspaced Short Palindromic Repeats (CRISPR) guide ribonucleic acids (gRNA), or any combination thereof.

In some embodiments, the encapsulated agent is a bacteriocin or a modified derivative thereof. In some embodiments, the bacteriocin is selected from the group consisting of colicin, diffocin, pyocin, and rhuricin 17.

In some embodiments, the encapsulated agent is an autolysin, an endolysin, an antimicrobial peptide, an antitoxin, or any combination thereof.

In some embodiments, the encapsulated shell is modified with an antibody. In some embodiments, the antibody targets intestinal epithelial cells.

In some embodiments, the spore secretion system produces encapsulated agents. In some embodiments, the encapsulated agents induce germination of spores. In some embodiments, the encapsulated agents are bile salts. In some embodiments, the encapsulated agent is a protease.

In some embodiments, the microbe further comprises a microbe death trigger.

In some embodiments, the composition is a probiotic, a food, a nutraceutical, a pharmaceutical, a biospray and/or a beverage. In some embodiments, the composition further comprises a pharmaceutically acceptable carrier/excipient.

In some embodiments, the pathogenic microbe is part of a population of cultured cells (i.e., in vitro). In some embodiments, the pathogenic microbe is part of a population of cells of a subject (i.e., in vivo).

In some embodiments, the state is a virulent state. In other embodiments, the state is a spore state.

In some embodiments, the pathogenic infection is a recurrent pathogenic infection.

In some embodiments, the pathogen infection is caused by an intestinal and/or gastrointestinal pathogen, for example, *Clostridium difficile*.

In some embodiments, the subject experiences and/or reports fewer or less severe side effects on natural gut microbiota as compared to a conventional therapy, for example, the conventional therapy is an antibiotic.

In some embodiments, the genetically engineered microbes are locally administered.

In some embodiments, the composition comprising genetically engineered microbes is administered sequentially or concurrently with an antibiotic. In some embodiments, the composition is administered after the antibiotic.

DETAILED DESCRIPTION

Figure 1:
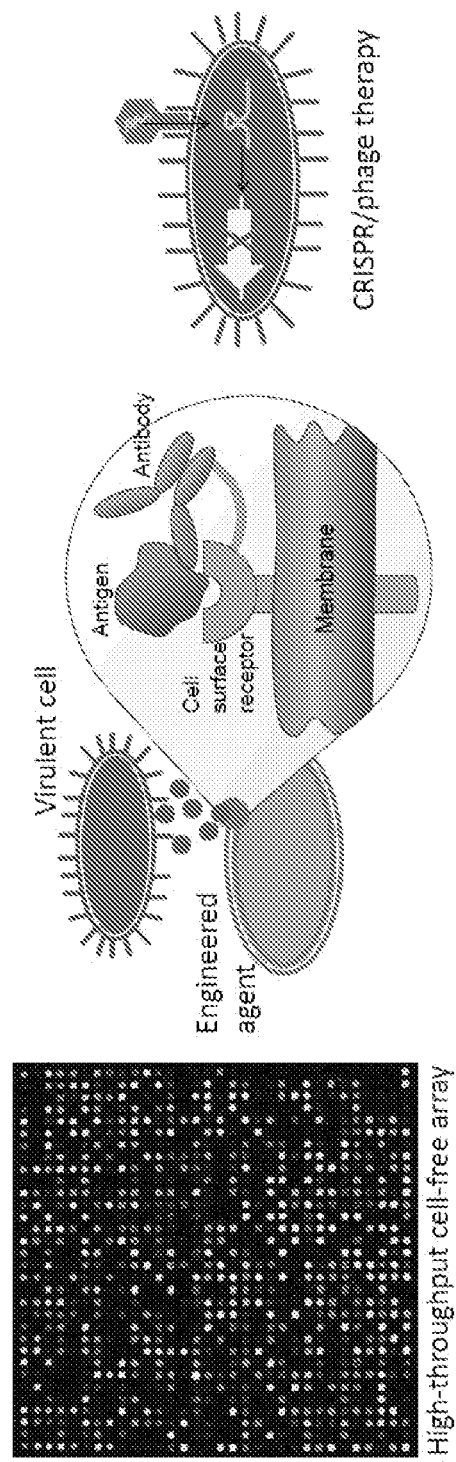
FIG. 1 presents a schematic of the screening process of cell binding domains/antibodies, endolysins and antimicrobial peptides for developing engineered cell surface signaling receptors that have virulent binding domains and that initiate release of a CRISPR/phage therapy that target and kill pathogens.

Conventional treatments for pathogenic infections often utilize broad spectrum antibiotics. Such antibiotics, like ampicillin for example, revolutionized medicine for their ability to act against a wide range of disease causing bacteria. However, these antibiotics indiscriminately target both the pathological bacteria and the natural, beneficial microbiota. Destruction of the body's natural bacteria provides an environment for drug resistant microbes to prosper and lead to secondary infection. One common secondary infection is C. diff. Importantly, use of "silver bullet" antibiotics as a single treatment regimen often does not meet all the requirements for efficacy, drug delivery, and low host toxicity. In particular, pathogens adapt and evolve to these static treatments such that the treatments become ineffective.

The present disclosure relates to the use of live therapeutic agents (i.e., genetically engineered microbes) that can dynamically sense and respond to the current state of a pathogen. Using multiple mechanisms of attack, these agents act, in part, to slow down the evolution of resistance. These therapeutic agents can be specifically tailored to identify and respond to a particular pathogen and can be locally released to minimize the effects on the host's tissue and natural microbiota.

After reading this description it will become apparent to one skilled in the art how to implement the invention in various alternative embodiments and alternative applications. However, all the various embodiments of the present invention will not be described herein. It will be understood that the embodiments presented here are presented by way of example only, and not limitation. As such, this detailed description of various alternative embodiments should not be construed to limit the scope or breadth of the present invention as set forth below.

The detailed description is divided into various sections only for the reader's convenience and disclosure found in any section may be combined with that in another section. Titles or subtitles may be used in the specification for the convenience of a reader, which are not intended to influence the scope of the present disclosure.

The practice of the present disclosure will employ, unless otherwise indicated, conventional techniques of tissue culture, immunology, molecular biology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); McPherson et al. (1991) PCR 1: A Practical Approach (IRL Press at Oxford University Press); McPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (2002) Cold Spring Harbor Laboratory Press; Sohail (2004) Gene Silencing by RNA Interference: Technology and Application (CRC Press).

Unless the context indicates otherwise, it is specifically intended that the various features of the invention described herein can be used in any combination. Moreover, the disclosure also contemplates that in some embodiments any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

It must be noted that as used herein and in the appended claims, the singular forms "a," "an," and "the" include plural referents unless the context clearly dictates otherwise. Thus, for example, reference to "a cell" includes a plurality of cells.

Definitions

As used herein the following terms have the following meanings:

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein the term "operatively connected," such as in reference to a sensor for detection of a pathogen and a secretion system means the sensor and the secretion system are connected in such a way that they work together, for example, via cell signaling. The elements that are operatively connected do not need to actually touch, but one element acts on the other.

Microbes

Aspects of the disclosure provide genetically engineered microbes. Suitable microbes include, for example, bacteria (e.g., *Lactobacillus*), yeast (e.g., *Saccharomyces* and *Candida*), and algal. In some embodiments, the microbe is a bacterium, for example a Gram-positive or a Gram-negative bacterium.

Non-limiting examples of suitable bacteria include *Acetobacter* spp., *Acidithiobacillus* spp., *Aeromonas* spp., *Agrobacterium* spp., *Alcaligenes* spp., *Arthrobacter* spp., *Azotobacter* spp., *Bacillus* spp., *Chromobacterium* spp., *Citrobacter* spp., *Clostridium* spp., *Comamonas* spp., *Corynebacterium* spp., *Escherichia* spp., *Flavobacterium* spp., *Geobacillus* spp., *Geobacter* spp., *Gluconobacter* spp., *Lactobacillus* spp., *Lactococcus* spp., *Microlunatus* spp., *Mycobacterium* spp., *Pantoea* spp., *Pseudomonas* spp., *Ralstonia* spp., *Rhizobium* spp., *Rhodococcus* spp., *Saccharopolyspora* spp., *Salmonella* spp., *Serratia* spp., *Sinorhizobium* spp., *Stenotrophomonas* spp., *Streptococcus* spp., *Streptomyces* spp., *Synechocystis* spp., *Thermus* spp., *Xanthomonas* spp., and *Zymonas* spp.

In some embodiments, the bacterium is a probiotic. Probiotics are live microorganisms, which when administered in adequate amounts confer a health benefit on the host. Non-limiting examples of probiotic bacteria include *Escherichia coli Nissle* 1917, *Lactococcus Lactis*, *Lactobacillus Acidophilus*, *Lactobacillus Brevis*, *Lactobacillus Bulgaricus*, *Lactobacillus Casei*, *Lactobacillus Helveticus*, *Lactobacillus reuteri*, *Lactobacillus rhamnosus*, *Lactobacillus Rhamnosus* GG, *Lactobacillus rhamnosus* GR-1, *Lactobacillus plantarum*, *Lactobacillus Silivarius*, *Eubacterium hallii* and *Bifidobacterum Bifidum*, *Bifidobacterum Breve*, *Bifidobacterium Infantis*, *Bifidobacterium Lactis*, *Bifidobacterium longum*, *Bacillus Coagulans*, *Saccharomyces Boulardii*, *Streptococcus Thermophilus* or a combination thereof. In one preferred embodiment, the bacteria is *Lactococcus Lactis* (*L. lactis*).

Non-limiting examples of suitable yeast include *Brettanomyces* spp., *Candida* spp., *Debaryomyces* spp., *Kluyveromyces* spp., *Pachysolen* spp., *Paffia* spp., *Pichia* spp., *Saccharomyces* spp., *Schizosaccharmoyces* spp., *Talaromyces* spp., and *Yarrowia* spp. In one embodiment, the yeast is a modified *Saccharmoyces cerevisiae*.

In some embodiments, the microbe is a viable microbe.

Engineered Microbes

Aspects of the disclosure encompass genetically engineered microbe comprising a pathogen state detection system, in particular a dual pathogen state detection system. The detection systems comprise a sensor on the surface of the microbe that detects the presence of a pathogen. Detection can occur directly (i.e., detection of a pathogen cell surface marker) or indirectly (i.e., detection of a signal produced by the pathogen (e.g., a toxin). In a preferred embodiment, the dual pathogen state detection system of the microbes comprise at least a first sensor for detection of a virulent form of a pathogen and a second sensor for detection of a spore form of the pathogen. The terms "state" and "form" can be used interchangeably in reference to a pathogen. For example, the spore state is equivalent to the spore form.

In some embodiments, at least the first sensor or the second sensor detects a protein on the surface of the pathogen. In other embodiments, the first sensor detects a protein on the surface of the pathogen and the second sensor detects a non-surface pathogen signal. In yet other embodiments, the second sensor detects a protein on the surface of the pathogen and the first sensor detects a non-surface pathogen signal. In still other embodiments, both the first sensor and the second sensor detect a protein on the surface of the pathogen.

In some embodiments, the first sensor, the second sensor, or both is a modified cell surface receptor. A cell surface receptor can be modified by any method known in the art. Non-limiting examples of modified cell surface receptors include antibodies, endolysins, and antimicrobial peptides, and fragments thereof. In some embodiments, the modified cell surface receptor comprises an antibody, antimicrobial peptide, or fragment thereof.

In one embodiment, the antibody or fragment thereof is a monoclonal antibody. In another embodiment, the antibody is a polyclonal. Suitable antibodies or fragments thereof for use with the present disclosure include, for example, actoxumab, bezlotoxumab, anthem, pagibaximab, efibazumab, urtoxazumab. As used herein the term "antibody" or "antibodies" refers to immunoglobulin molecules and immunologically active portions or immunoglobulin molecules (i.e., molecules that contain an antigen binding site that immune-specifically bind an antigen). The term also refers to antibodies comprise of two immunoglobulin heavy chains and two immunoglobulin light chains as well as any variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFV, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavechhia et al., (1987) *Eur. J Immunol.* 17, 105) and single chains (e.g., Huston et al., *Proc. Natl. Acad Sci. U.S.A.*, (1988) 85, 5879-5883 and Bird et al., (1988) *Science* 242, 423-426, which are incorporated herein by reference). (See, generally, Hood et al., Immunology, Benjamin, N.Y., 2ND ed. (1984); Harlow and Lane, Antibodies. A Laboratory Manual, Cold Spring Harbor Laboratory (1988); Hunkapiller and Hood, (1986) *Nature,* 323, 15-16, which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric.

Antimicrobial peptides (AMPs) are a component of the innate immune system and play a critical role in warding off invading pathogens. To date, more than 2,500 peptides have been isolated and characterized. Wang et al, (2004) *Nucleic Acids Res.* 32(Database issue): D590-2. Suitable AMPS include, for example, HBD1-3, HNP1, HD5 cathelicidins (e.g., LL-37), coprisin, polymixin, and nisin.

In one preferred embodiment, at least one of the first sensor or the second sensor does not detect a quorum sensing molecule. A quorum sensing molecule refers to a molecule produced by a cell that can signal population density of the population of cells containing that cell. In some embodiments, a quorum sensing molecule is an oligopeptide, an N-Acyl homoserine lactone (AHL), an autoinducer or a pheromone.

Virulent Detection and Secretion System

The disclosure provides a first sensor for detection of a virulent form of a pathogen, wherein the first sensor is operatively connected to a virulent secretion system.

In some embodiments, the first sensor detects a compound, for example a toxin, secreted from the pathogen. Bacterial generate toxins which are classified as exotoxins or endotoxins. Exotoxins are secreted, while endotoxins remain part of the bacteria. In some embodiments, the first sensor detects large clostridial toxins (LCTs) produced by *Clostridium difficile, Clostridium sordellii, Clostridium perfringens,* or *Clostridium novyi*. In some embodiments, the toxin is *C. difficile* toxin A (TcdA), toxin B (TcdB), or binary toxin A (CDTa). Toxin A is an enterotoxin that causes diarrhea. Toxin B is a cytotoxin that kills cells.

Other non-limiting examples of bacterial toxins include, *Bordetella pertussis* AC toxin (A/B) and *Bacillus anthracis* EF, *Botulinum* neurotoxin (BoNT), tetanus toxin (TeNT protein), staphylococcal toxin, alpha toxin, anthrax toxin, cholera toxin, cyanotoxin, diphtheria toxin, *E. coli* heat-labile toxin LT, pertussis toxin, *Pseudomonas* toxin A, shiga toxin, shiga-like toxin, and *Staphylococcus aureus* Exfoliatin B.

In some embodiments, the first sensor detects a cell surface protein on the surface of the virulent pathogen. In some embodiments, the cell surface protein is Cwp66 adhesin protein, S-layer proteins (e.g., HMW-SLP), or flagellin protein (e.g., FlaA, FlgE). In some embodiments, the cell surface protein is a spore coat proteins, for example, BclA glycoproteins or CdeC.

In some embodiments, the first sensor detects a catalytic or cell wall binding domain of *C. difficile*. In some embodiments, the catalytic or cell wall binding domain from *C. difficile* includes any one of SEQ ID NOS. 1-36 or a portion thereof.

In some embodiments, the first sensor detects a catalytic or cell wall binding domain of *Clostridium phages*. In some embodiments, the catalytic or cell wall binding domain from *Clostridium phages* includes any one of SEQ ID NOS. 37-40 or a portion thereof.

In one preferred embodiment, first sensor for detection of a virulent form of a pathogen does not detect a quorum sensing molecule.

The microbes of the present disclosure also provide a virulent secretion system which is operatively connected to the first sensor.

The virulent secretion system can produce one or more agents in an encapsulated shell, one or more Clustered Regularly Interspaced Short Palindromic Repeats (CRISPR) guide ribonucleic acids (gRNA), or any combination thereof. An example of CRISPR targets include Frizzled proteins (as described in Tao et al. (2016) *Nature* 538:350-355. In some embodiments, the CRISPR target is a toxin gene, for example, TcdA or TcdB. In some embodiments, the encapsulated agent is a bacteriocin, such as, colicin, diffocin, pyocin, and rhuricin 17, or a modified derivative thereof. In other embodiments, the encapsulated agent is an autolysin, an endolysin, an antimicrobial peptide, an antitoxin, or any combination thereof.

The encapsulation shells can be created by any method known in the field, for example, by the method described by Moon et al. (2014) which is hereby incorporated by reference in its entirety. Moon et al. (2014) *Biomacromolecules* 15 (10), 3794-3801. The encapsulation shells can be modified by any known method. For example, the encapsulated shell is modified with an antibody. In one embodiment, the antibody targets intestinal epithelial cells.

Spore Detection and Secretion System

The disclosure also provides a second sensor for detection of a spore form of the pathogen, wherein the second sensor is operatively connected to a spore secretion system.

In some embodiments, the second sensor detects a cell surface protein on the spore pathogen, for example, a cell wall protein or a spore coat protein. Non-limiting examples of spore coat proteins include a BclA glycoprotein and a cysteine (CdeC)-rich protein.

In one preferred embodiment, the second sensor for detection of a spore form of a pathogen does not detect a quorum sensing molecule.

The microbes of the present disclosure also provide a spore secretion system which is operatively connected to the second sensor. In some embodiments, the spore secretion system produces encapsulated agents.

In some embodiments, wherein the encapsulated agents induce germination of spores, for example, bile salts. In other embodiments, the encapsulated agent is a protease.

In some embodiments, the microbes disclosed herein further comprise a microbe death trigger (e.g., a suicide cassette). Cells may contain suicide cassettes comprising inserted sequences encoding certain reporter proteins (e.g., thymidine kinase (TK)). In some embodiments, suicide cassettes are used to facilitate the identification of cells from a larger cell population. In other embodiments, suicide cassettes are used to destroy microbes which have proliferated to an undesirable level in vivo. Microbes can be further modified to comprise a tracking system to follow the in vivo position and ultimately final location and/or clearance of the microbes following introduction into a subject. For example, the engineered microbes may be modified to comprise a fluorescent detectable marker (e.g., green fluorescent protein (GFP)).

The microbes of the present disclosure can be genetically modified by any suitable methodology. As a non-limiting example, one or more of the nucleic acids (e.g., nucleic acid encoding for the first sensor, the second sensor, the virulent secretion system, and/or the spore secretion system) associated with the disclosure can be expressed in a recombinant expression vector. As used herein, a "vector" may be any of a number of nucleic acids into which a desired sequence or sequences may be inserted, such as by restriction and ligation, for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which can be further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired nucleic acid sequence may be inserted, for example by restriction and ligation, such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined. When the nucleic acid molecule that encodes any of the genes associated with the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

Expression vectors containing all the necessary elements for expression are commercially available and known to those skilled in the art. See, e.g., Sambrook et al., Molecular Cloning: A Laboratory Manual, Fourth Edition, Cold Spring Harbor Laboratory Press, 2012. Cells are genetically engineered by the introduction into the cells of heterologous DNA (RNA). That heterologous DNA (RNA) is placed under operable control of transcriptional elements to permit the expression of the heterologous DNA in the host cell. A nucleic acid molecule that comprises a gene associated with the invention can be introduced into a cell or cells using methods and techniques that are standard in the art.

A nucleic acid, polypeptide or fragment thereof described herein can be synthetic. As used herein, the term "synthetic" means artificially prepared. A synthetic nucleic acid or polypeptide is a nucleic acid or polypeptide that is synthesized and is not a naturally produced nucleic acid or polypeptide molecule (e.g., not produced in an animal or organism). It will be understood that the sequence of a natural nucleic acid or polypeptide (e.g., an endogenous nucleic acid or polypeptide) may be identical to the sequence of a synthetic nucleic acid or polypeptide, but the latter will have been prepared using at least one synthetic step.

Compositions

The disclosure also provides compositions comprising an amount of the genetically engineered microbes disclosed and described herein. In some embodiments, the composition is a probiotic, a food, a nutraceutical, a pharmaceutical, a biospray and/or a beverage.

In some embodiments, the composition further comprises a pharmaceutically acceptable carrier/excipient. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The composition may comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Compositions may be prepared using conventional techniques that may include sterile isotonic saline, water, 1,3-butanediol, ethanol, 1,2-propylene glycol, polyglycols mixed with water, Ringer's solution, etc. In one aspect, a coloring agent is added to facilitate in locating and properly placing the composition to the intended treatment site.

Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

To control tonicity, the composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Compositions may include one or more buffers. Typical buffers include: a phosphate buffer, a Tris buffer, a borate buffer, a succinate buffer, a histidine buffer, or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

The genetically engineered microbes may be formulated in a composition for oral administration, for example, as a tablet, capsule, or drink. The genetically engineered microbes may be combined in a liquid carrier. Preferably, the liquid carrier is a moving fluid and the term "liquid carrier" refers to any liquid suitable for ingestion and includes pharmaceutical formulations and foodstuffs such as water, milk, fruit juices, vegetable juices, electrolytic beverages and the like.

The composition can comprise one or more additional substances that can be consumed by the genetically engineered microbe to keep the relevant microbe alive or stimulate its growth. Non-limiting examples of additional substances include mucopolysaccharides, oligosaccharides, polysaccharides, amino acids, vitamins, nutrient precursors and proteins The composition can be included in an implantable device. Suitable implantable devices contemplated by this invention include encapsulation, scaffolds, grafts, and the like. Such implantable devices can be coated on at least one surface, impregnated, or encapsulated with a composition disclosed and described herein.

Methods of Use

Also provided are methods for killing or inhibiting a pathogenic microbe comprising delivering the genetically engineered microbe as disclosed and described herein to a composition comprising the pathogenic microbe. In some embodiments, the pathogenic microbe is a bacterial pathogen, a viral pathogen, or a fungal pathogen.

In some embodiments, the pathogenic microbe is part of a population of cultured cells (i.e., in vitro). In other embodiments, the pathogenic microbe is part of a population of cells of a subject (i.e., in vivo).

Also provided herein are methods of detecting a state (e.g., virulent or spore) of a pathogenic microbe comprising delivering the genetically engineered microbe as disclosed and described herein to a composition comprising the pathogenic microbe. In some embodiments, the pathogenic microbe is part of a population of cultured cells (i.e., in vitro). In other embodiments, the pathogenic microbe is part of a population of cells of a subject (i.e., in vivo).

Also provided herein are methods of treating or preventing a pathogenic infection in a subject in need thereof comprising administering to the subject an effective amount of a composition comprising genetically engineered microbes as disclosed and described herein.

Subjects treated by the methods disclosed herein include, a simian, a bovine, an equine, a canine, a murine, or a human patient.

In some embodiments, the pathogenic infection is a recurrent pathogenic infection.

In one embodiment, the compositions described herein are useful in treating bacterial infections. Infectious bacteria include, without limitation, *Bacillus* spp.; *Bordetella* spp.; *Borrelia* spp.; *Brucella* spp.; *Burkholderia* spp.; *Campylobacter* spp.; *Chlamydia* spp.; *Chlamydophila* spp.; *Clostridium* spp.; *Corynebacterium* spp.; *Enterococcus* spp.; *Escherichia* spp.; *Francisella* spp.; *Haemophilus* spp.; *Helicobacter* spp.; *Legionella* spp.; *Leptospira* spp.; *Listeria* spp.; *Mycobacterium* spp.; *Mycoplasma* spp.; *Neisseria* spp.; *Pseudomonas* spp.; *Rickettsia* spp.; *Salmonella* spp.; *Shigella* spp.; *Staphylococcus* spp.; *Streptococcus* spp.; *Treponema* spp.; *Vibrio* spp.; and *Yersinia* spp. In one embodiment, the bacterial pathogen is a *Clostridium difficile* (C. diff). In some embodiments, the bacterial pathogen is an antibiotic-resistant bacterial pathogen. In some embodiments, the bacterial pathogen is a hypervirulent strain.

Non-limiting examples of diseases caused by bacterial pathogens include acute enteritis, anthrax, bacterial meningitis, botulism, brucellosis, cholera, community-acquired respiratory infection, diptheria, dysentery, hemolytic-uremic syndrome, hemorrhagic colitis, leprosy, lyme disease, lymphogranuloma venereum, neumonia, nongonococcal urethritis, sepsis, syphilis (e.g., congenital syphilis), tetanus, tuberculosis, typhoid fever, whooping cough, trachoma, inclusion conjunctivitis of the newborn, psittacosis, pseudomembranous colitis, gas gangrene, food poisoning, anaerobic cellulites, nosocomial infections, urinary tract infections, diarrhea, tularemia, upper respiratory tract infections, bronchitis, peptic ulcers, legionnaire's disease, pontiac fever, leptospirosis, listeriosis, tuberculosis, gonorrhea, ophthalmia neonatorum, septic arthritis, meningococcal disease, Waterhouse-Friderichsen syndrome, *Pseudomonas* infection, rocky mountain spotted fever, typhoid fever type salmonellosis (dysentery, colitis), Salmonellosis with gastroenteritis and/or enterocolitis, bacillary dysentery/Shigellosis, coagulase-positive staphylococcal infections (such as impetigo, acute infective endocarditis, septicemia, necrotizing pneumonia, and toxinoses such as toxic shock syndrome or Staphylococcal food poisoning), cystitis, septicemia, endometritis, otitis media, sinusitis, Streptococcal pharyngitis, scarlet fever, rheumatic fever, erysipelas, puerperal fever, necrotizing fasciitis, bubonic plague and pneumonic plague.

In some embodiments, the pathogen infection is caused by an intestinal and/or gastrointestinal pathogen. Gastrointestinal pathogens include pathogens (e.g., bacteria) that can colonize in the gut of a subject and cause and/or do cause a disease or condition in the subject. Exemplary gastrointestinal pathogens include, but are not limited to *Escherichia coli, Clostridium difficile, Clostridium perfringens, Listeria monocytogenes, Listeria innocua, Staphylococcus aureus, Enterococcus faecalis* (virulent strains of *E. faecalis*), and *Enterococcus faecium*.

In one embodiment, the compositions described herein are useful in treating infections by pathogenic viruses. Pathogenic viruses include, without limitation, human papillomavirus, human immunodeficiency virus, Epstein-Barr virus, cytomegalovirus, Ebola virus, Marburg virus, influenza, respiratory syncytial virus, poxvirus, varicella-zoster virus, and herpes.

Non-limiting examples of viral pathogens include viruses belonging to the following families: Adenoviridae (e.g., adenovirus), Picornaviridae (e.g., coxsackievirus, hepatitis A virus, poliovirus and rhinovirus), Herpesviridae (e.g., herpes simplex type 1, herpes simplex type 2, Varicella-zoster virus, Epstein-barr virus, human cytomegalovirus, and human herpesvirus type 8), Hepadnaviridae (e.g., hepatitis B virus), Flaviviridae (e.g., hepatitis C virus, yellow fever virus, dengue virus, and West Nile virus), Retroviridae (e.g., human immunodeficiency virus (HIV)), Orthomyxoviridae (e.g., influenza virus), Paramyxoviridae (e.g., measles virus, mumps virus, parainfluenza virus, respiratory syncytial virus and human metapneumovirus), Papillomaviridae (e.g., papillomavirus), Rhabdoviridae (e.g., rabies virus), Togaviridae (e.g., ubella virus) and Parvoviridae (e.g., human bocavirus and parvovirus B19).

Non-limiting examples of diseases caused by viral pathogens include: acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection, gingivostomatitis, tonsillitis, pharyngitis, primary HSV-2 infection, latent HSV-2 infection, aseptic meningitis, infectious mononucleosis, cytomegalic inclusion disease, Kaposi's sarcoma, Castleman disease, primary effusion lymphoma, AIDS, influenza, Reye syndrome, measles, postinfectious encephalomyelitis, mumps, hyperplastic epithelial lesions, laryngeal papillomas, epidermodysplasia verruciformis, croup, pneumonia, bronchiolitis, common cold, rabies, German measles, congenital rubella, varicella and herpes zoster.

The microbial compositions described herein are useful in treating infections caused by other microbes, including fungus and yeast Cells can be administered to such an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$, (and so forth) cells per administration, or any ranges between any two of the numbers, end points inclusive. In other embodiments, cells can be administered to such an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) cells per kilogram of the individual, or any ranges between any two of the numbers, end points inclusive. In some embodiments, between about 1 billion and about 3 billion cells are administered to a patient. In other embodiments, the total dose may be calculated based on m$^2$ of body surface area, including $11\times10^{11}$, $1\times10^{10}$, $1\times10^9$, $1\times10^8$, $1\times10^7$, per m$^2$. The average person is 1.6-1.8 m$^2$.

In one embodiment, the pathogenic infection is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or 100% as compared to baseline or a control group receiving a conventional therapy.

In one embodiment, the pathogenic infection is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or 100% as compared to baseline or a control group receiving a conventional therapy within about 1 day, about 2 days, about 3 days, about 4 days, about 5 days, about 6 days, about 1 week, about 2 weeks, about 3 weeks, about 4 weeks, about 2 months, about 3 months, about 4 months, about 6 months, about 1 year after administering a first dose of the genetically engineered microbes.

In one embodiment, the subject who is administered the genetically engineered microbes experiences and/or reports fewer or less severe side effects on natural gut microbiota as compared to baseline or a control group receiving a conventional therapy. Any method known in the art for assessing natural gut microbiota can be used. Suitable methods include a hydrogen breath test or analyzing a bacterial culture of the small intestine or a stool sample.

In one embodiment, the subject administered the genetically engineered microbe experiences and/or reports fewer or less severe symptoms as compared to baseline or a control group receiving a conventional therapy. Non-limiting examples of symptoms include, fever, pain in abdomen, fatigue, loss of appetite, headache, dry tongue, rice water diarrhea, diarrhea, severe diarrhea with vomiting, slow pulse, cold and clammy skin, dry tongue, severe dehydration, low blood pressure, loss of weight, persistent cough, weakness, occasional blood in sputum, chest pain, burning in urine, painful urination, discharge of pus, yellow or green sputum, pain in chest while coughing, rapid pulse, excessive perspiration, running nose, throat pain, sneezing, itching and burning in nose and eyes, vomiting, muscle pain, rash, itching, or any combination thereof.

Non-limiting examples of conventional therapies for a pathogenic infection include antibacterial drugs (e.g., penicillins, cephalosporins, macrolides, and fluoroquinolones), antiviral drugs (e.g., amantadine, rimantadine, oseltamivir, and zanamivir), and anti-fungal medication (e.g., clotrimazole, econazole nitrate, miconazole, terbinafine, fluconazole, ketoconazole, amphotericin). In some embodiments, the conventional therapy is erythromycin, clindamycin, rifamycin, or any combination thereof.

The composition can be administered by any appropriate route, which will be apparent to the skilled person depending on the disease or condition to be treated. Typical routes of administration include oral, topical, intravenous, intra-arterial, intramuscular, subcutaneous, intracranial, intranasal or intraperitoneal. The composition can be administered by another (e.g., a physician or healthcare provider) or self-administered. In one embodiment, the composition can be administered topically. In another embodiment, the composition can be administered via injection. In a preferred embodiment, the composition can be administrated orally. The terms "oral", "enteral", "enterally", "orally", "non-parenteral", "non-parenterally", and the like, refer to administration of a cell or composition to an individual by a route or mode along the alimentary canal. Examples of "oral" routes of administration of a microbe composition include, without limitation, swallowing liquid or solid forms of a microbe composition from the mouth, administration of a microbe composition through a nasojejunal or gastrostomy tube, intraduodenal administration of a microbe composition, and rectal administration, e.g., using suppositories that release a live microbe described herein to the lower intestinal tract of the alimentary canal.

The composition may also be directly delivered in any manner directly into the gastrointestinal tract. In one embodiment, it is delivered downstream of the stomach directly into the intestines. In another include: (1) placement of a percutaneous endoscopic gastrostomy (PEG) tube and passing a weighted or non-weighted feeding tube into the duodenum or jejunum; (2) surgically placing a direct jejunostomy tube; or, (3) placing a tube directly into the jejunum with a known PEG-like procedure, whereby the jejunum is accessed by stab-piercing the jejunum from outside the abdominal wall.

The dosage and frequency of administration may depend on the type of formulation, route of administration, disease being treated, the amount of cells and any combination therapies, the subject's age, weight, gender, species, other conditions, and the like.

In some embodiments, the composition comprising genetically engineered microbes is administered sequentially or concurrently with an antibiotic. In some embodiments, the genetically engineered microbes are administered after a period of time following administration of an antibiotic. In some embodiments, the subject stops taking the antibiotic prior to administration of the microbes.

EXAMPLES

Example 1: Pathogen-Detecting Sensor Technology

A sensor technology that can turn any specific antibody or binding domain into a cell surface signal will be developed. The antibody or binding domains will be fused to existing cell-surface receptor proteins (i.e., two-component signaling receptors, chemotaxis receptors, quorum sensing circuits) and the fusion proteins will be expressed on the surface of the microbe. FIG. 1. The binding of a pathogen-specific ligand to the antibody or binding domain will either (1) block or disable the binding site of the original receptor, turning the ligand binding into an OFF switch for the chosen signaling circuit or (2) induce a conformational change in the receptor to turn binding into an ON switch. The binding event will then transduce a signal to drive specific transcriptional responses and subsequent expression of specific effectors, for example, a bacteriocin or a protease. Orthogonal binding domains will be designed for specific toxins and surface proteins. Targets include toxins TcdA and TcdB, which are secreted by the virulent form of *C. difficile*, and spore coat proteins (i.e., BclA glycoproteins and cysteine-rich CdeC). Tying such a sensor to a chemotaxis pathway will allow the engineered microbes to "swim" toward virulent pathogens.

In addition, an infectious pathogen's own sensors can be targeted. Here, a pathogen genome will be mined for sensors of its own environmentally secreted molecules (e.g., quorum sensing receptors). For example, microbes can be engineered to intercept *C. difficile* siderophores, iron scavenging molecules, to sense the presence of the pathogen and, at the same time, deprive the pathogen of an essential resource.

Example 2: Targeted Countermeasures Against Virulent Pathogen Cells

Microbes will be engineered to produce countermeasures to kill, disable or modify the behavior of the virulent pathogen. Multiple proteins have been identified during a computational screen for native autolysins and *C. difficile* phage endolysins that may be able to specifically degrade the cell wall of virulent *C. difficile* to lyse the pathogen. As some of these lysin proteins are native proteins that play an essential role in cell division, it would be difficult for the pathogen to evolve resistance to them. Proteins identified by the screen include those encoded by SEQ ID NOS. 1-40.

Candidate lysin proteins will be screened by high-throughput, cell-free synthesis on a protein array to identify those that show cell-killing activity against *C. difficile* but not the engineered microbes of the disclosure. Antimicrobial peptides can also be screened for specific activity in killing *C. difficile*. Effective lysins/peptides can be expressed and secreted upon sensing the presence of the target pathogen. Alternatively, effective lysins/peptides can be produced in an encapsulated form in order to prevent potential toxicity to the host therapeutic agent. To release the encapsulated proteins, the engineered microbe will turn on expression of a bacteriophage lytic protein upon pathogen detection. In addition to the lysins/peptides, encapsulated antitoxins can also be releases to mitigate the effects of the virulent toxins, for example, upon host tissues. The encapsulated shells can be modified with antibodies for targeting to epithelial cells.

Microbes can also be engineered to deliver toxin-specific CRISPR guide RNA (gRNA) to disarm virulent *C. difficile*. Upon detection of virulent *C. difficile*, the prophage will be triggered to enter the lytic cycle, cause cell lysis of the engineered microbes and release the phage. The phage can subsequently deliver the CRISPR gRNA to the virulent cell and effectively edit the virulent cell genome to disable the toxin tcdA/B genes, converting the bacterium to a non-virulent form. The presence of non-toxin producing *C. difficile* can inhibit growth of the virulent form. Nagaro et al., (2013) *Antimicrob. Agents Chemother.* 57(11):5266-5270. Therefore, by producing more non-virulent *C. difficile*, it is contemplated that suppression of the virulent form will be stimulated.

Example 3: Targeted Countermeasures Against the Spore State

As a first strategy to selectively kill the highly resistant but dormant *C. difficile* spores, specific proteases that cleave spore coat proteins will be used. An example of one such target is the cysteine-rich protein CdeC, which has been shown to be essential for assembly of the exosporium layer. Paredes-Sabja et al., (2014) *Trends Microbiol.* 22(7):406-416. Encapsulated proteases can be delivered, via host microbe lysis, in which the encapsulin shell is targeted to CdeC to provide specificity of cleavage. As a second strategy, microbes can be engineered to metabolize primary bile salts into deoxycholate, which has been shown to induce germination in *C. difficile* and also inhibit growth of the cells after germination. Sorg et al., (2008) *J. Bacteriol.* 190 (7):2505-2512. By activating "sleeper" spores, the spores become visible and vulnerable to the arsenal of agents the engineered microbes use to target the virulent state of the pathogen.

Figure 2:
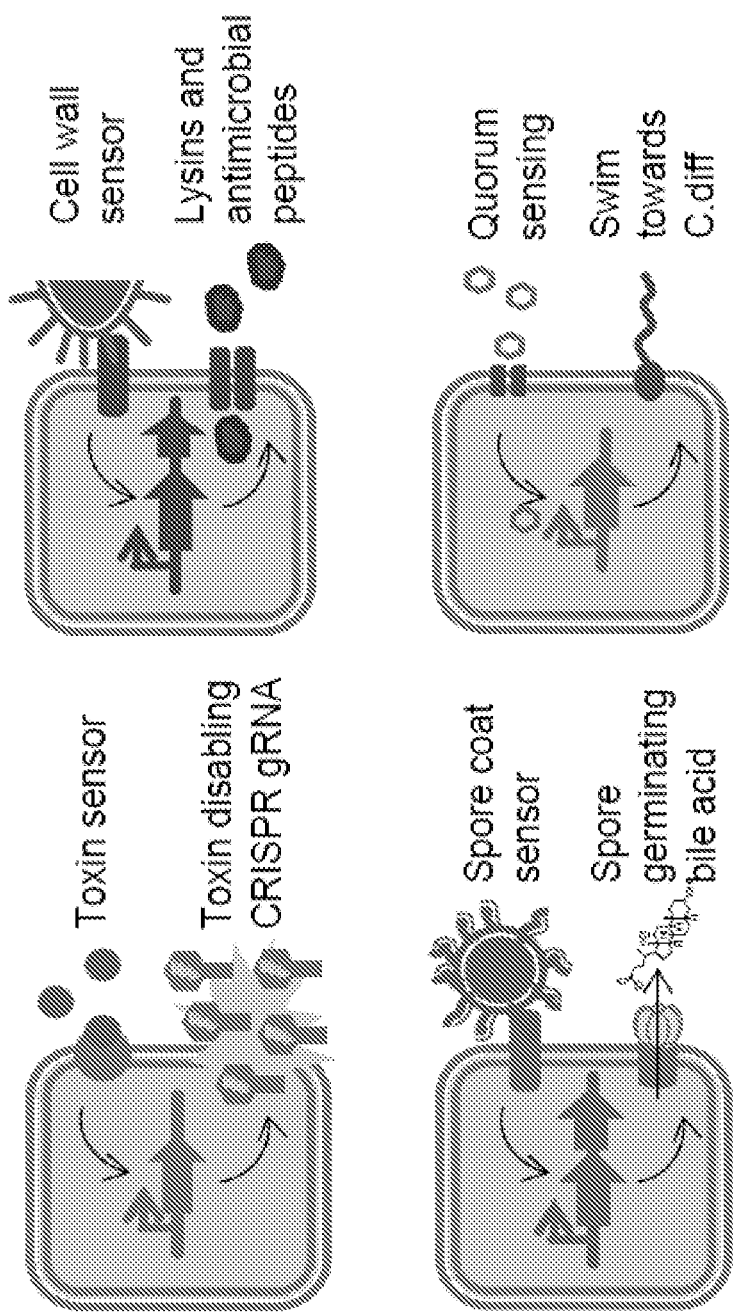
FIG. 2 presents several schematics of modular pathogen state detection systems according to an embodiment of the present disclosure.

Example 4: Engineered Microbes to Dynamically Adapt and Respond to the Pathogen and Host State Each countermeasure/agent produced by the engineered microbes to target the pathogen can be deployed under the control of an appropriate sensor. For example, the secretion of CRISPR-loaded phages to knockout the pathogen toxin genes can be under control of a toxin sensor, while the secretion of spore coat degrading proteases can be under the control of a spore coat sensor. Each of the feedback loops can be engineered independently (FIG. 2) and in parallel into multiple initial strains of the genetically engineered microbes and dose-response characteristics can be fine-tuned through the choice of suitable transcription factors (TFs), multiplicity of TF binding sites, and autoregulation. Ang et al., (2013) *ACS Synth Biol.* 2:547-567. It is preferred that responses that involve cell lysis of the engineered microbe be have an all-or-nothing response, so only a fraction of the cells commit suicide. Eldar et al. (2010)

Figure 3:
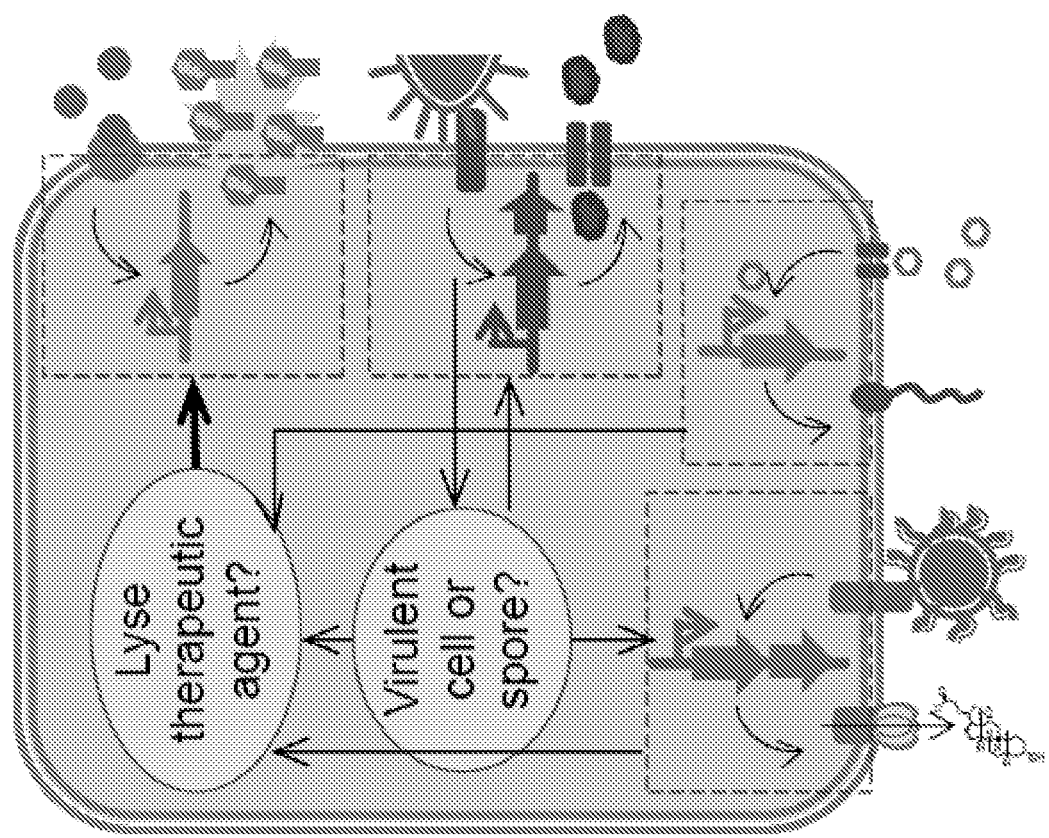
FIG. 3 presents a schematic of a therapeutic microbe according to an embodiment of the present disclosure, engineered to detect and respond to both virulent and spore forms of a pathogen and to calculate when and whether to undergo lysis to release a therapeutic agent.
Figure 4:
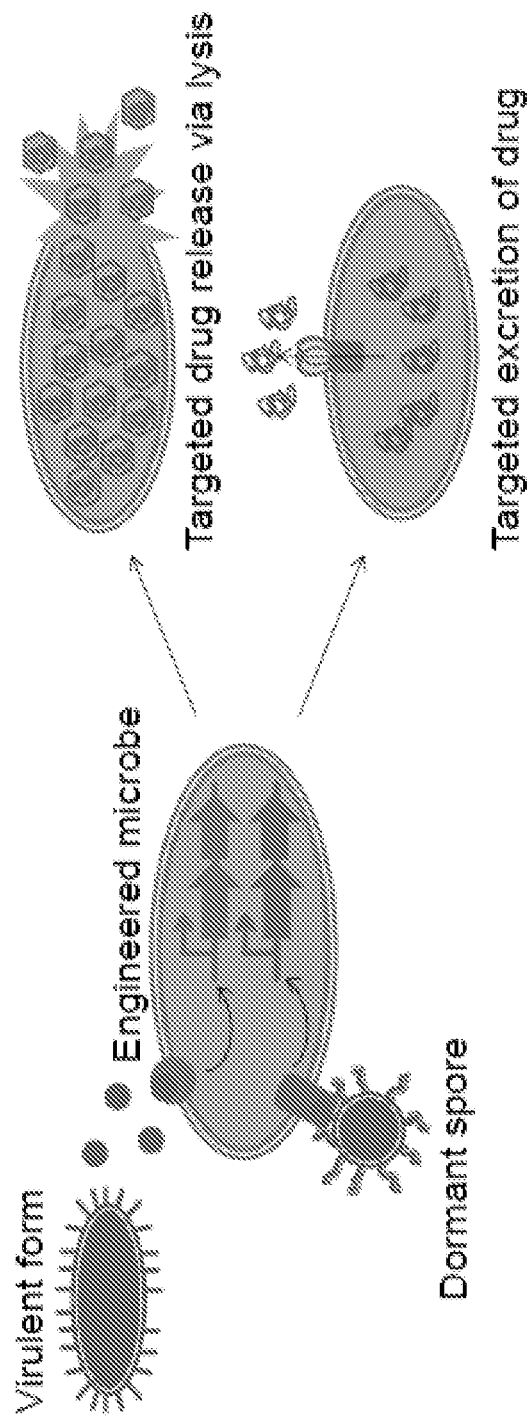
FIG. 4 presents a schematic of a therapeutic agent according to an embodiment of the present disclosure, engineered to sense the changing state of a pathogen within a host, process the information using engineered signaling cascades, and deliver specific, scalable, and effective countermeasures against the sensed state. Upon detection of a spore coat protein on the surface of the dormant spore form, the engineered microbe releases a spore-targeting agent. Upon binding of a toxin (circles) released from the virulent form, the engineered microbe releases via lysis an encapsulated virulent targeting agent.

Nature 467:167-173. Once each sensor-countermeasure system has been fine-tuned individually, systems can be combined into a single engineered microbe, with some additional regulatory logic to integrate across sensor inputs and response pathways. FIG. 3 and FIG. 4

Figure 5:
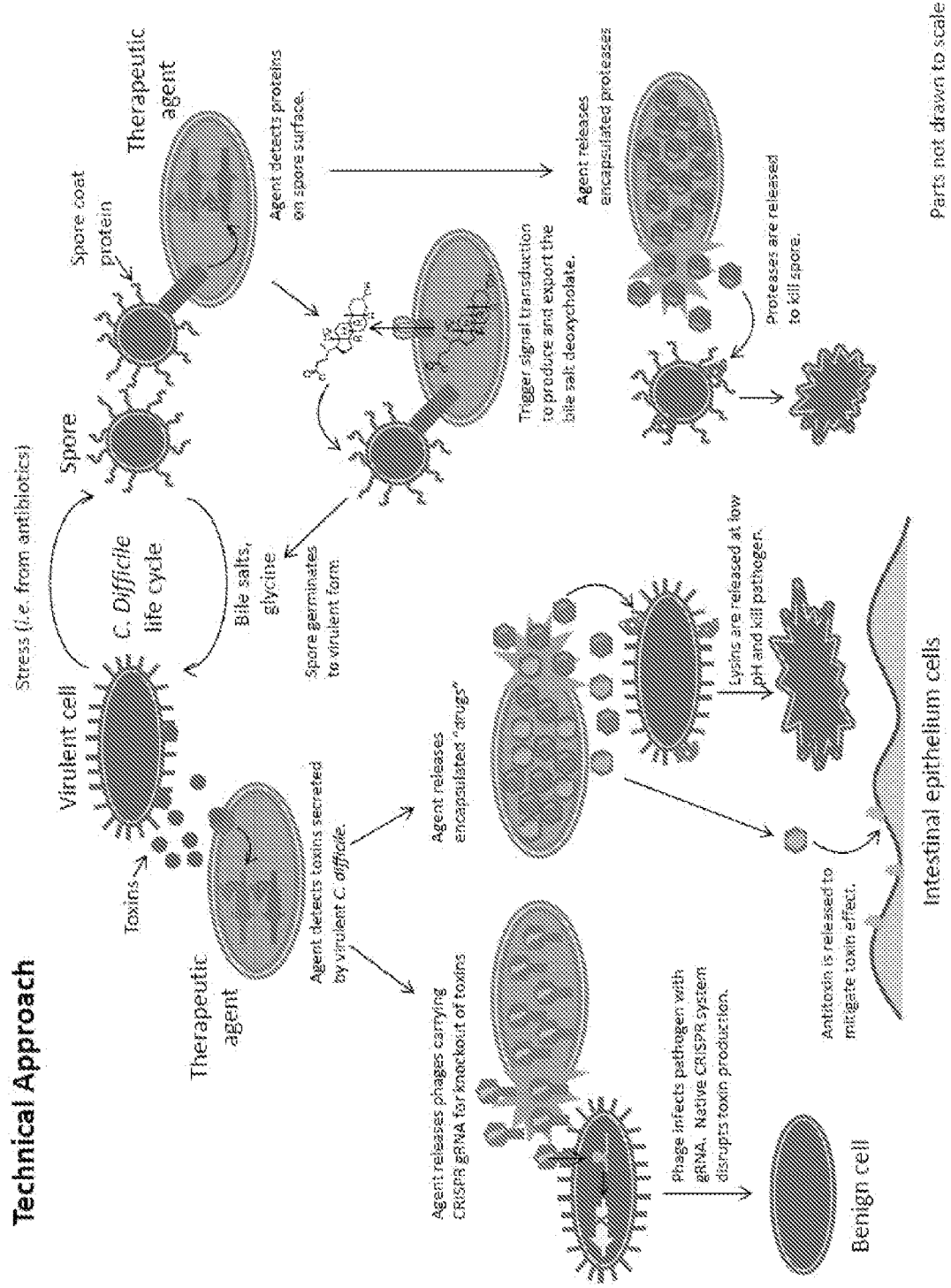
FIG. 5 presents a general schematic of a dynamically adaptive therapeutic agent according to an embodiment of the present disclosure, engineered to be able to detect and respond to both spore and virulent forms of *C. difficile*, as well as mitigate toxic effect of toxin on host tissues.

FIG. 5 shows an example of a dynamically adaptive therapeutic microbe according to an embodiment of the present disclosure that senses both *C. difficile* spores and virulent cells (i.e., contains a virulent sensor linked to a virulent secretion system and a spore sensor linked to spore section system). The therapeutic microbe/agent has been engineered to detect spore coat proteins. Binding of the spore coat protein to the sensor on the therapeutic agent triggers: (1) signal transductions to cause the therapeutic agent to secrete a compound that induces spores to germinate into a virulent form, for example, a bile salt or (2) release of encapsulated proteases that bind to and kill the *C. difficile* spores. The therapeutic agent also detects toxins released by the virulent cells. The toxins bind to the virulent sensor on the cell surface of the engineered microbe and activate expression of virulent agents. For example, the engineered microbe can release phages carrying CRISPR gRNA for knockout of toxins whereby the phage infects the *C. difficile* pathogen and the native CRISPR system disrupts the toxin production to result in a benign *C. difficile*. In addition, the engineered microbe can release encapsulated drugs, for example lysins. The lysins are released at low pH and kill the pathogenic *C. difficile*. Finally, the engineered microbe can release encapsulated antitoxins to mitigate the toxin effect on host tissue (e.g., intestinal epithelium cells).

Example 5: Validation of Engineered Microbes

In vitro tests involving a simple two-bacterial system with the engineered microbe and *C. difficile*, both virulent and spore forms, will be performed. Microscopy and flow cytometry will be utilized to examine how effective the engineered microbes are in neutralizing both forms of *C. difficile*. Next, combining the engineered microbes in a controlled microbiome, including non-virulent *C. difficile* and other gut microbes, the changes in the microcosm composition will be measured using next-generation sequencing.

Animal cell lines that are commonly used to model human intestinal disease, for example Caco-2 and HT-29, will be introduced to the engineered microbes to assess the toxicity and efficacy of the microbes in the presence of host cells. Using in vivo animal studies, the engineered microbes will be administered, with and without other gut microbes, after an antibiotic treatment course in mice infected by virulent *C. difficile*. The health state of the mice will be monitored and the gut microbiome will be analyzed from the fecal microbiota using next generation sequencing.

Finally, in silico computer modeling will be employed to simulate the population dynamics of the microbiome. Data from experimental in vitro and in vivo studies will be incorporated. A conceptual model will be formulated for the native behavior of the gut microbiome during recolonization after broad spectrum antibiotic treatment, with and without the presence of *C. difficile*, and the tipping point for the onset of *C. difficile* infection will be identified. Influence of the engineered microbes will then be incorporated into the system. Using these models, the impact of changing given factors (e.g., inoculum size and death rate) to the system will be predicted in order to assess the effectiveness of the engineered microbes and predict the evolutionary behavior of the gut microbiome components of interest.

What is claimed is:

1. A genetically engineered viable *Lactobacillus* or *Lactococcus* probiotic bacterium comprising a dual pathogen state detection system, the dual pathogen detection system comprising:

a first sensor for detection of a large clostridial toxin (LCT) secreted by a virulent form of *Clostridium difficile* (C. diff), wherein the first sensor is operatively connected to a virulent secretion system, wherein the virulent secretion system produces one or more agents in an encapsulated shell and a second sensor for detection of a cell surface protein on a spore form of C. diff, wherein the second sensor is operatively connected to a spore secretion system, wherein the spore secretion system produces an encapsulated agent.

2. The genetically engineered probiotic bacterium of claim 1, wherein the first sensor is an antibody or a functionally active epitope binding fragment thereof that immunospecifically binds to the large clostridial toxin and the second sensor is an antibody or an epitope binding fragment thereof that immunospecifically binds to the cell surface protein.

3. The genetically engineered probiotic bacterium of claim 2, wherein the antibody is a monoclonal antibody or a polyclonal antibody.

4. The genetically engineered probiotic bacterium of claim 1, wherein the large clostridial toxin is *C. difficile* toxin A (TcdA) or *C. difficile* toxin B (TcdB).

5. The genetically engineered probiotic bacterium of claim 1, wherein the cell surface protein is a spore coat protein of *C. difficile*.

6. The genetically engineered probiotic bacterium of claim 5, wherein the spore coat protein is the BclA glycoprotein or the cysteine-rich protein CdeC.

7. The genetically engineered probiotic bacterium of claim 1, wherein the one or more agents in the encapsulated shell is an endolysin.

8. The genetically engineered probiotic bacterium of claim 1, wherein the one or more agents in the encapsulated shell is a bacteriocin selected from the group consisting of colicin, diffocin, pyocin, and rhuricin 17.

9. The genetically engineered probiotic bacterium of claim 1, wherein the encapsulated agent induces germination of the spore.

10. The genetically engineered probiotic bacterium of claim 1, wherein the encapsulated agent is a bile salt or a protease.

* * * * *

SEQUENCE LISTING

```
<160> NUMBER OF SEQ ID NOS: 40

<210> SEQ ID NO 1
<211> LENGTH: 675
<212> TYPE: PRT
<213> ORGANISM: Clostridium difficile

<400> SEQUENCE: 1

Met Met Lys Lys Thr Thr Lys Leu Leu Ala Thr Gly Met Leu Ser Val
1               5                   10                  15

Ala Met Val Ala Pro Asn Val Ala Leu Ala Ala Glu Asn Thr Thr Ala
            20                  25                  30

Asn Thr Glu Ser Asn Ser Asp Ile Asn Ile Asn Leu Gln Arg Lys Ser
        35                  40                  45

Val Val Leu Gly Ser Lys Ser Asn Ala Ser Val Lys Phe Lys Glu Lys
    50                  55                  60

Leu Asn Ala Asp Ser Ile Thr Leu Asn Phe Met Cys Tyr Asp Met Pro
65                  70                  75                  80

Leu Glu Ala Thr Leu Asn Tyr Asn Glu Lys Thr Asp Ser Tyr Glu Gly
                85                  90                  95

Val Ile Asn Tyr Asn Lys Asp Pro Glu Tyr Leu Asn Val Trp Glu Leu
            100                 105                 110

Gln Ser Ile Lys Ile Asn Gly Lys Asp Glu Gln Lys Val Leu Asn Lys
        115                 120                 125

Glu Asp Leu Glu Ser Met Gly Leu Asn Leu Lys Asp Tyr Asp Val Thr
    130                 135                 140
```

```
Gln Glu Phe Ile Ile Ser Asp Ala Asn Ser Thr Lys Ala Val Asn Glu
145                 150                 155                 160

Tyr Met Arg Lys Thr Ser Ala Pro Val Lys Leu Ala Gly Ala Thr
            165                 170                 175

Arg Phe Glu Thr Ala Val Glu Ile Ser Lys Gln Gly Trp Lys Asp Gly
            180                 185                 190

Ser Ser Lys Val Val Ile Val Asn Gly Glu Leu Ala Ala Asp Gly Ile
            195                 200                 205

Thr Ala Thr Pro Leu Ala Ser Thr Tyr Asp Ala Pro Ile Leu Leu Ala
210                 215                 220

Asn Lys Asp Asp Ile Pro Glu Ser Thr Lys Ala Glu Leu Lys Arg Leu
225                 230                 235                 240

Asn Pro Ser Asp Val Ile Ile Gly Asp Asp Gly Ser Val Ser Gln
                245                 250                 255

Lys Ala Val Ser Gln Ile Lys Ser Ala Val Asn Val Asn Val Thr Arg
                260                 265                 270

Ile Gly Gly Val Asp Arg His Glu Thr Ser Leu Leu Ile Ala Lys Glu
            275                 280                 285

Ile Asp Lys Tyr His Asp Val Asn Lys Ile Tyr Ile Ala Asn Gly Tyr
            290                 295                 300

Ala Gly Glu Tyr Asp Ala Leu Asn Ile Ser Ser Lys Ala Gly Glu Asp
305                 310                 315                 320

Gln Gln Pro Ile Ile Leu Ala Asn Lys Asp Ser Val Pro Gln Gly Thr
                325                 330                 335

Tyr Asn Trp Leu Ser Ser Gln Gly Leu Glu Ala Tyr Tyr Ile Gly
            340                 345                 350

Gly Ser Gln Ser Leu Ser Ser Lys Ile Ile Asp Gln Ile Ser Lys Ile
            355                 360                 365

Ala Lys Asn Gly Thr Ser Lys Asn Arg Val Ser Gly Ala Asp Arg His
    370                 375                 380

Glu Thr Asn Ala Asn Val Ile Lys Thr Phe Tyr Pro Asp Lys Glu Leu
385                 390                 395                 400

Ser Ala Met Leu Val Ala Lys Ser Asp Ile Val Asp Ser Ile Thr
                405                 410                 415

Ala Gly Pro Leu Ala Ala Lys Leu Lys Ala Pro Ile Leu Ile Thr Pro
            420                 425                 430

Lys Thr Tyr Val Ser Ala Tyr His Ser Thr Asn Leu Ser Glu Lys Thr
            435                 440                 445

Ala Gly Thr Val Tyr Gln Ile Gly Asp Gly Met Lys Asp Ser Val Ile
    450                 455                 460

Asn Ser Ile Ala Ser Ser Leu Ser Lys His Asn Ala Pro Thr Glu Pro
465                 470                 475                 480

Asp Asn Ser Gly Ser Ala Ala Gly Lys Thr Val Val Ile Asp Pro Gly
            485                 490                 495

His Gly Gly Ser Asp Ser Gly Ala Thr Ser Gly Leu Asn Gly Gly Ala
            500                 505                 510

Gln Glu Lys Lys Tyr Thr Leu Asn Thr Ala Leu Ala Thr Glu Tyr
            515                 520                 525

Leu Arg Ser Lys Gly Ile Asn Val Val Met Thr Arg Asp Thr Asp Lys
    530                 535                 540

Thr Met Ala Leu Gly Glu Arg Thr Ala Leu Ser Asn Thr Ile Lys Pro
545                 550                 555                 560
```

```
Asp Leu Phe Thr Ser Ile His Tyr Asn Ala Ser Asn Gly Ala Gly Asn
            565                 570                 575

Gly Val Glu Ile Tyr Tyr Lys Val Lys Asp Lys Asn Gly Gly Thr Thr
        580                 585                 590

Lys Thr Ala Ala Ser Asn Ile Leu Lys Arg Ile Leu Glu Lys Phe Asn
        595                 600                 605

Met Lys Asn Arg Gly Ile Lys Thr Arg Thr Leu Asp Asn Gly Lys Asp
    610                 615                 620

Tyr Leu Tyr Val Leu Arg Asn Asn Asn Tyr Pro Ala Ile Leu Val Glu
625                 630                 635                 640

Cys Ala Phe Ile Asp Asn Lys Ser Asp Met Asp Lys Leu Asn Thr Ala
                645                 650                 655

Glu Lys Val Lys Thr Met Gly Thr Gln Ile Gly Ile Gly Ile Glu Asp
        660                 665                 670

Thr Val Lys
        675

<210> SEQ ID NO 2
<211> LENGTH: 679
<212> TYPE: PRT
<213> ORGANISM: Clostridium difficile

<400> SEQUENCE: 2

Met Leu Ser Lys Glu Ile Asn Met Arg Arg Asn Thr Lys Leu Leu Thr
1               5                   10                  15

Thr Gly Ile Leu Ser Met Ala Ile Val Thr Pro Thr Met Ala Phe Ala
            20                  25                  30

Thr Glu Ser Asn Ala Met Glu Asn Asn Ala Asp Leu Asn Ile Asn Leu
        35                  40                  45

Glu Lys Lys Ser Ile Val Leu Gly Ser Thr Ser Lys Val Ser Val Lys
    50                  55                  60

Phe Lys Glu Lys Pro Asp Ala Asp Ser Ile Thr Leu Lys Tyr Lys Cys
65                  70                  75                  80

Tyr Asp Met Pro Leu Asp Thr Thr Leu Asn Tyr Asn Gln Ser Thr Glu
                85                  90                  95

Ser Tyr Glu Gly Thr Ile Asn Tyr Asn Lys Asp Pro Glu Tyr Leu Asn
            100                 105                 110

Val Trp Glu Leu Gln Gly Ile Thr Ile Asn Ser Lys Asn Asn Pro Lys
        115                 120                 125

Thr Leu Asn Lys Gln Glu Leu Glu Lys Met Gly Leu Asn Leu Lys Asp
    130                 135                 140

Tyr Asn Val Thr Gln Glu Cys Ile Ile Glu Asp Ile Thr Ser Arg Lys
145                 150                 155                 160

Asp Val Asn Lys Tyr Leu Arg Lys Thr Ser Ala Pro Ile Thr Glu Leu
                165                 170                 175

Thr Gly Ser Asp Arg Tyr Glu Thr Ala Val Lys Ile Ser Lys Glu Gly
            180                 185                 190

Trp Lys Asn Gly Ser Asp Lys Val Val Ile Ile Asn Gly Asp Val Ser
        195                 200                 205

Ile Asp Gly Ile Ile Ser Thr Pro Leu Ala Thr Thr Tyr Asn Ala Pro
    210                 215                 220

Ile Leu Leu Val Glu Lys Asn Asn Val Pro Asn Ser Val Lys Ser Glu
225                 230                 235                 240

Leu Lys Arg Leu Asn Pro Arg Asp Val Ile Ile Ile Gly Asp Glu Asn
                245                 250                 255
```

```
Ala Ile Ser Lys Thr Thr Ala Asn Gln Ile Lys Ser Thr Val Asn Ala
        260                 265                 270

Ser Gln Thr Arg Leu Lys Gly Ser Asn Arg Tyr Glu Thr Ser Leu Leu
            275                 280                 285

Ile Ala Lys Glu Ile Asp Lys Asn His Asp Val Glu Lys Val Tyr Ile
        290                 295                 300

Thr Asn Ala Asn Gly Gly Glu Val Asp Ala Leu Thr Ile Ala Ala Lys
305                 310                 315                 320

Ala Gly Gln Asp Lys Gln Pro Ile Ile Leu Thr Asp Lys Asn Ser Ile
                325                 330                 335

Thr Asp Asn Thr Tyr Lys Trp Leu Lys Ser Glu Asp Leu Gln Asn Ala
            340                 345                 350

Tyr Phe Ile Gly Gly Pro Gln Met Ile Ser Thr Asn Val Ile Asn Lys
        355                 360                 365

Val Asn Asp Ile Thr Lys Asp Asn Val Thr Asn Asn Arg Val Tyr Gly
    370                 375                 380

Ala Asp Arg His Glu Thr Asn Ala Asn Val Ile Lys Lys Phe Tyr Thr
385                 390                 395                 400

Asp Asp Glu Leu Glu Ala Val Leu Val Ala Lys Ser Asp Val Leu Val
            405                 410                 415

Asp Ala Leu Ala Ala Gly Pro Leu Ala Ala Asn Leu Lys Ser Pro Ile
        420                 425                 430

Leu Ile Thr Pro Lys Thr Tyr Val Ser Ala Tyr His Lys Glu Asn Leu
        435                 440                 445

Glu Ala Lys Ser Ala Asn Lys Val Tyr Lys Ile Gly Gly Gly Leu Thr
    450                 455                 460

Ser Lys Val Met Ser Ser Ile Ala Ser Ser Leu Ser Lys His Asn Thr
465                 470                 475                 480

Thr Pro Thr Glu Pro Gly Asn Ser Gly Gly Lys Thr Val Met Ile Asp
            485                 490                 495

Pro Gly His Gly Gly Ser Asp Thr Gly Thr Thr Gly Lys Pro Leu Gly
        500                 505                 510

Gly Ile Arg Glu Lys Asp Tyr Thr Leu Asn Thr Ser Leu Ala Thr Thr
        515                 520                 525

Glu Tyr Leu Arg Ser Lys Gly Phe Asn Val Ile Met Thr Arg Asp Thr
    530                 535                 540

Asp Lys Thr Leu Ser Leu Gly Asn Arg Thr Ala Leu Ser Asn Ser Leu
545                 550                 555                 560

Arg Pro Asp Leu Phe Thr Ser Ile His Tyr Asn Ala Ser Asp Thr Thr
                565                 570                 575

Gly Asn Gly Val Glu Val Phe Tyr Lys Leu Lys Asp Lys Asp Gly Gly
            580                 585                 590

Thr Thr Lys Thr Val Ala Thr Asn Ile Leu Asn Arg Ile Leu Glu Lys
        595                 600                 605

Phe Asn Leu Lys Asn Arg Gly Ala Lys Thr Arg Thr Leu Ser Thr Asp
    610                 615                 620

Pro Thr Lys Asp Tyr Leu Tyr Val Leu Arg Asn Asn Asp Met Pro Ala
625                 630                 635                 640

Val Leu Val Glu Cys Ala Phe Leu Asp Asn Glu Lys Asp Met Ser Leu
                645                 650                 655

Leu Asn Thr Ser Asn Lys Val Lys Glu Met Gly Thr Gln Ile Gly Lys
            660                 665                 670
```

```
Gly Ile Glu Asp Ser Leu Lys
        675
```

```
<210> SEQ ID NO 3
<211> LENGTH: 319
<212> TYPE: PRT
<213> ORGANISM: Clostridium difficile

<400> SEQUENCE: 3

Met Ile Ser Thr Asn Val Ile Asn Lys Val Asn Gly Ile Thr Lys Asp
1               5                   10                  15

Asn Val Thr Asn Asn Arg Val Tyr Gly Ala Asp Arg His Glu Thr Asn
            20                  25                  30

Ala Asn Val Ile Lys Lys Phe Tyr Thr Asp Asp Glu Leu Glu Ala Ile
        35                  40                  45

Leu Val Ala Lys Ser Asp Val Leu Val Asp Ala Leu Ala Ala Gly Pro
    50                  55                  60

Leu Ala Ala Ser Leu Lys Ser Pro Ile Leu Ile Thr Pro Lys Thr Tyr
65                  70                  75                  80

Val Ser Ala Tyr His Lys Thr Asn Leu Glu Thr Lys Ser Ala Asn Lys
                85                  90                  95

Val Tyr Lys Ile Gly Gly Gly Leu Thr Ser Lys Val Met Ser Ser Ile
            100                 105                 110

Ala Ser Ser Leu Ser Lys His Asn Thr Thr Pro Ala Asp Pro Gly Ser
        115                 120                 125

Asn Asn Gly Ala Lys Thr Val Met Ile Asp Pro Gly His Gly Gly Ser
    130                 135                 140

Ala Pro Gly Asn Ser Phe Gly Gly Met Ile Glu Lys Asp Tyr Asn Leu
145                 150                 155                 160

Asn Thr Ser Leu Ala Thr Thr Glu Tyr Leu Arg Ser Lys Asp Ile Asn
                165                 170                 175

Val Ile Met Thr Arg Asp Thr Asp Lys Thr Leu Ser Leu Gly Ser Arg
            180                 185                 190

Thr Ala Leu Ser Asn Ser Leu Lys Pro Asp Leu Phe Thr Ser Ile His
        195                 200                 205

Tyr Asn Gly Asp Asn Asn Arg Lys Gly His Gly Val Glu Val Phe Tyr
    210                 215                 220

Lys Phe Lys Asp Lys Asn Gly Gly Thr Thr Lys Thr Val Ala Thr Asn
225                 230                 235                 240

Ile Leu Asn Arg Ile Leu Glu Lys Phe Lys Leu Thr Asn Arg Gly Ile
                245                 250                 255

Lys Thr Arg Val Leu Pro Ser Asp Ser Thr Lys Asp Tyr Leu Tyr Val
            260                 265                 270

Leu Arg Thr Asn Asn Ile Pro Ala Val Leu Val Glu Cys Ala Phe Leu
        275                 280                 285

Asp Asn Glu Lys Asp Val Ser Leu Ile Asn Ser Pro Ala Lys Val Lys
    290                 295                 300

Glu Met Gly Ile Gln Ile Gly Lys Gly Ile Glu Asp Ser Leu Lys
305                 310                 315
```

```
<210> SEQ ID NO 4
<211> LENGTH: 422
<212> TYPE: PRT
<213> ORGANISM: Clostridium difficile

<400> SEQUENCE: 4
```

```
Ser Ile Ser Lys Thr Thr Ala Asn Gln Ile Lys Ser Thr Ile Asn Ala
1               5                   10                  15

Thr Gln Thr Arg Leu Asn Gly Ser Asn Arg Tyr Glu Thr Ser Leu Leu
            20                  25                  30

Ile Ala Lys Glu Ile Asp Lys Asn His Asp Val Glu Lys Val Tyr Ile
            35                  40                  45

Thr Asn Ala Asn Gly Gly Glu Val Asp Ala Leu Thr Ile Ala Ala Lys
50                  55                  60

Ala Gly Gln Asp Lys Gln Pro Ile Ile Leu Thr Asp Lys Asp Ser Ile
65                  70                  75                  80

Thr Asp Asn Thr Ser Lys Trp Leu Glu Asn Glu Asp Leu Gln Asn Ala
                85                  90                  95

Tyr Phe Ile Gly Gly Pro Gln Met Ile Ser Thr Asn Val Ile Asn Lys
            100                 105                 110

Val Asn Gly Ile Thr Lys Asp Asn Val Thr Asn Asn Arg Val Tyr Gly
            115                 120                 125

Ala Asp Arg His Glu Thr Asn Ala Asn Val Ile Lys Lys Phe Tyr Thr
    130                 135                 140

Asp Asp Glu Leu Glu Ala Ile Leu Val Ala Lys Ser Asp Val Leu Val
145                 150                 155                 160

Asp Ala Leu Ala Ala Gly Pro Leu Ala Ala Ser Leu Lys Ser Pro Ile
                165                 170                 175

Leu Ile Thr Pro Lys Thr Tyr Val Ser Ala Tyr His Lys Thr Asn Leu
            180                 185                 190

Glu Thr Lys Ser Ala Asn Lys Val Tyr Lys Ile Gly Gly Gly Leu Thr
            195                 200                 205

Ser Lys Val Met Ser Ser Ile Ala Ser Leu Ser Lys His Asn Thr
210                 215                 220

Thr Pro Ala Asp Pro Gly Ser Asn Asn Gly Ala Lys Thr Val Met Ile
225                 230                 235                 240

Asp Pro Gly His Gly Gly Ser Ala Pro Gly Asn Ser Phe Gly Gly Met
                245                 250                 255

Ile Glu Lys Asp Tyr Asn Leu Asn Thr Ser Leu Ala Thr Thr Glu Tyr
            260                 265                 270

Leu Arg Ser Lys Asp Ile Asn Val Ile Met Thr Arg Asp Thr Asp Lys
            275                 280                 285

Thr Leu Ser Leu Gly Ser Arg Thr Ala Leu Ser Asn Ser Leu Lys Pro
290                 295                 300

Asp Leu Phe Thr Ser Ile His Tyr Asn Gly Asp Asn Arg Lys Gly
305                 310                 315                 320

His Gly Val Glu Val Phe Tyr Lys Phe Lys Asp Lys Asn Gly Gly Thr
            325                 330                 335

Thr Lys Thr Val Ala Thr Asn Ile Leu Asn Arg Ile Leu Glu Lys Phe
            340                 345                 350

Lys Leu Thr Asn Arg Gly Ile Lys Thr Arg Val Leu Pro Ser Asp Ser
            355                 360                 365

Thr Lys Asp Tyr Leu Tyr Val Leu Arg Thr Asn Asn Ile Pro Ala Val
            370                 375                 380

Leu Val Glu Cys Ala Phe Leu Asp Asn Glu Asp Val Ser Leu Ile
385                 390                 395                 400

Asn Ser Pro Ala Lys Val Lys Glu Met Gly Ile Gln Ile Gly Lys Gly
                405                 410                 415

Ile Glu Asp Ser Leu Lys
```

<210> SEQ ID NO 5
<211> LENGTH: 281
<212> TYPE: PRT
<213> ORGANISM: Clostridium difficile

<400> SEQUENCE: 5

Ile Ser Lys Thr Thr Ala Asn Gln Ile Lys Ser Thr Val Asn Ala Ser
1               5                   10                  15

Gln Thr Arg Leu Asn Gly Ser Asn Arg Tyr Glu Thr Ser Leu Leu Ile
            20                  25                  30

Ala Lys Glu Ile Asp Lys Asn His Asp Val Lys Val Tyr Ile Thr
        35                  40                  45

Asn Ala Asn Gly Gly Glu Val Asp Ala Leu Thr Ile Ala Ala Lys Ala
    50                  55                  60

Gly Gln Asp Lys Gln Pro Ile Ile Leu Thr Asp Lys Asp Ser Ile Thr
65                  70                  75                  80

Asp Asn Thr Tyr Lys Trp Leu Lys Ser Glu Asp Leu Gln Asn Ala Tyr
                85                  90                  95

Phe Ile Gly Gly Pro Gln Met Ile Ser Thr Asn Val Ile Asn Lys Val
            100                 105                 110

Asn Gly Ile Thr Lys Asp Ser Val Thr Asn Asn Arg Val Tyr Gly Ala
        115                 120                 125

Asp Arg His Glu Thr Asn Ala Asn Val Ile Lys Lys Phe Tyr Thr Ala
130                 135                 140

Asp Glu Leu Glu Ala Val Leu Val Ala Lys Ser Asp Val Leu Val Asp
145                 150                 155                 160

Ala Leu Ala Ala Gly Pro Leu Ala Ala Asn Leu Lys Ser Pro Ile Leu
                165                 170                 175

Ile Thr Pro Lys Thr Tyr Val Ser Ala Tyr His Lys Gly Asn Leu Glu
            180                 185                 190

Ala Lys Ser Ala Asn Lys Val Tyr Lys Ile Gly Gly Gly Leu Thr Ser
        195                 200                 205

Lys Val Met Ser Ser Ile Ala Ser Ser Leu Ser Lys His Asn Thr Thr
210                 215                 220

Pro Thr Glu Pro Gly Asn Ser Gly Gly Lys Thr Val Met Ile Asp Pro
225                 230                 235                 240

Gly His Gly Gly Ser Ala Pro Gly Asn Ser Ser Gly Gly Met Ile Glu
                245                 250                 255

Lys Asp Tyr Asn Leu Asn Thr Ser Leu Ala Thr Thr Glu His Leu Arg
            260                 265                 270

Ser Lys Gly Phe Asn Val Ile Met Thr
        275                 280

<210> SEQ ID NO 6
<211> LENGTH: 320
<212> TYPE: PRT
<213> ORGANISM: Clostridium difficile

<400> SEQUENCE: 6

Met Ile Ser Thr Asn Val Ile Asn Lys Val Asn Gly Ile Thr Lys Asp
1               5                   10                  15

Ser Val Thr Asn Asn Arg Val Tyr Gly Ala Asp Arg His Glu Thr Asn
            20                  25                  30

Ala Asn Val Ile Lys Lys Phe Tyr Thr Asp Asp Glu Leu Glu Ala Val

```
                35                  40                  45
Leu Val Ala Lys Ser Asp Val Leu Val Asp Ala Leu Ala Ala Gly Pro
 50                  55                  60

Leu Ala Ala Asn Leu Lys Ser Pro Ile Leu Ile Thr Pro Lys Thr Tyr
 65                  70                  75                  80

Val Ser Ala Tyr His Lys Asp Asn Leu Glu Ala Lys Ser Ala Asn Lys
                 85                  90                  95

Val Tyr Lys Ile Gly Gly Gly Leu Thr Ser Lys Val Met Asn Ser Ile
                100                 105                 110

Ala Ser Ser Leu Ser Lys His Asn Thr Thr Pro Thr Glu Pro Gly Asn
            115                 120                 125

Ser Gly Gly Lys Thr Val Met Ile Asp Pro Gly His Gly Gly Ser Asp
130                 135                 140

Thr Gly Thr Thr Gly Lys Pro Leu Gly Gly Ile Lys Glu Lys Asp Tyr
145                 150                 155                 160

Thr Leu Asn Thr Ser Leu Ala Thr Thr Glu Tyr Leu Arg Ser Lys Gly
                165                 170                 175

Phe Asn Val Ile Met Thr Arg Asp Thr Asp Lys Thr Leu Ser Leu Gly
                180                 185                 190

Asn Arg Thr Ala Leu Ser Asn Ser Leu Arg Pro Asp Leu Phe Thr Ser
            195                 200                 205

Ile His Tyr Asn Ala Ser Asp Thr Thr Gly Asn Gly Val Glu Val Phe
210                 215                 220

Tyr Lys Leu Lys Asp Lys Asp Gly Gly Thr Thr Lys Thr Val Ala Thr
225                 230                 235                 240

Asn Ile Leu Asn Arg Ile Leu Glu Lys Phe Asn Leu Lys Asn Arg Gly
                245                 250                 255

Ala Lys Thr Arg Thr Leu Ser Thr Asp Pro Thr Lys Asp Tyr Leu Tyr
            260                 265                 270

Val Leu Arg Asn Asn Asp Met Pro Ala Val Leu Val Glu Cys Ala Phe
        275                 280                 285

Leu Asp Asn Glu Lys Asp Met Ser Leu Leu Asn Thr Ser Asn Lys Val
    290                 295                 300

Lys Glu Met Gly Thr Gln Ile Gly Lys Gly Ile Glu Asp Ser Leu Lys
305                 310                 315                 320

<210> SEQ ID NO 7
<211> LENGTH: 286
<212> TYPE: PRT
<213> ORGANISM: Clostridium difficile

<400> SEQUENCE: 7

Val Ile Lys Lys Phe Tyr Thr Asp Asp Glu Leu Glu Ala Val Leu Val
 1               5                  10                  15

Ala Lys Ser Asp Val Leu Val Asp Ala Leu Ala Ala Gly Pro Leu Ala
                20                  25                  30

Ala Asn Leu Lys Ser Pro Ile Leu Ile Thr Pro Lys Thr Tyr Val Ser
            35                  40                  45

Ala Tyr His Lys Glu Asn Leu Glu Ala Lys Ser Ala Asn Lys Val Tyr
        50                  55                  60

Lys Ile Gly Gly Gly Leu Thr Tyr Lys Val Met Asn Ser Ile Ala Ser
65                  70                  75                  80

Ser Leu Ser Lys His Asn Thr Thr Pro Thr Glu Pro Gly Asn Ser Gly
                85                  90                  95
```

```
Gly Lys Thr Val Met Ile Asp Pro Gly His Gly Ser Asp Thr Gly
            100                 105                 110

Thr Thr Gly Lys Pro Leu Gly Gly Ile Lys Glu Lys Asp Tyr Thr Leu
        115                 120                 125

Asn Thr Ser Leu Ala Thr Thr Glu Tyr Leu Arg Ser Lys Gly Phe Asn
130                 135                 140

Val Ile Met Thr Arg Asp Thr Asp Lys Thr Leu Ser Leu Gly Asn Arg
145                 150                 155                 160

Thr Ala Leu Ser Asn Ser Leu Arg Pro Asp Leu Phe Thr Ser Ile His
                165                 170                 175

Tyr Asn Ala Ser Asp Thr Thr Gly Asn Gly Val Glu Val Phe Tyr Lys
            180                 185                 190

Leu Lys Asp Lys Asp Gly Gly Thr Thr Lys Thr Val Ala Thr Asn Ile
        195                 200                 205

Leu Asn Arg Ile Leu Glu Lys Phe Asn Leu Lys Asn Arg Gly Ala Lys
210                 215                 220

Thr Arg Thr Leu Ser Thr Asp Pro Thr Lys Asp Tyr Leu Tyr Val Leu
225                 230                 235                 240

Arg Asn Asn Asp Met Pro Ala Val Leu Val Glu Cys Ala Phe Leu Asp
                245                 250                 255

Asn Glu Lys Asp Met Ser Leu Leu Asn Thr Ser Asn Lys Val Lys Glu
            260                 265                 270

Met Gly Thr Gln Ile Gly Lys Gly Ile Glu Asp Ser Leu Lys
        275                 280                 285

<210> SEQ ID NO 8
<211> LENGTH: 337
<212> TYPE: PRT
<213> ORGANISM: Clostridium difficile

<400> SEQUENCE: 8

Met Val Ser Ser Gln Gly Leu Glu Glu Ala Tyr Tyr Ile Gly Gly Ser
1               5                   10                  15

Gln Ser Leu Ser Ser Lys Ile Ile Asp Gln Ile Ser Lys Ile Ala Lys
            20                  25                  30

Asn Gly Thr Ser Lys Asn Arg Val Ser Gly Ala Asp Arg His Glu Thr
        35                  40                  45

Asn Ala Asn Val Ile Lys Thr Phe Tyr Pro Asp Lys Glu Leu Ser Ala
    50                  55                  60

Met Leu Val Ala Lys Ser Asp Ile Ile Val Asp Ser Ile Thr Ala Gly
65                  70                  75                  80

Pro Leu Ala Ala Lys Leu Lys Ala Pro Ile Leu Ile Thr Pro Lys Thr
                85                  90                  95

Tyr Val Ser Ala Tyr His Ser Thr Asn Leu Ser Glu Lys Thr Ala Glu
            100                 105                 110

Thr Val Tyr Gln Ile Gly Asp Gly Met Lys Asp Ser Val Ile Asn Ser
        115                 120                 125

Ile Ala Ser Ser Leu Ser Lys His Asn Ala Pro Thr Glu Pro Asp Asn
    130                 135                 140

Ser Gly Ser Ala Ala Gly Lys Thr Val Ile Asp Pro Gly His Gly Gly
145                 150                 155                 160

Gly Ser Asp Ser Gly Ala Thr Ser Gly Leu Asn Gly Ala Gln Glu
                165                 170                 175

Lys Lys Tyr Thr Leu Asn Thr Ala Leu Ala Thr Thr Glu Tyr Leu Arg
            180                 185                 190
```

```
Ser Lys Gly Ile Asn Val Val Met Thr Arg Asp Thr Asp Lys Thr Met
        195                 200                 205

Ala Leu Gly Glu Arg Thr Ala Leu Ser Asn Thr Ile Lys Pro Asp Leu
    210                 215                 220

Phe Thr Ser Ile His Tyr Asn Ala Ser Asn Gly Ala Gly Asn Gly Val
225                 230                 235                 240

Glu Ile Tyr Tyr Lys Val Lys Asp Lys Asn Gly Gly Thr Thr Lys Thr
                245                 250                 255

Ala Ala Ser Asn Ile Leu Lys Arg Ile Leu Glu Lys Phe Asn Met Lys
                260                 265                 270

Asn Arg Gly Ile Lys Thr Arg Thr Leu Asp Asn Gly Lys Asp Tyr Leu
            275                 280                 285

Tyr Val Leu Arg Asn Asn Asn Tyr Pro Ala Ile Leu Val Glu Cys Ala
        290                 295                 300

Phe Ile Asp Asn Lys Ser Asp Met Asp Lys Leu Asn Thr Ala Glu Lys
305                 310                 315                 320

Val Lys Thr Met Gly Thr Gln Ile Gly Ile Gly Ile Glu Asp Thr Val
                325                 330                 335

Lys
```

```
<210> SEQ ID NO 9
<211> LENGTH: 134
<212> TYPE: PRT
<213> ORGANISM: Clostridium difficile

<400> SEQUENCE: 9
```

```
Ile Lys Lys Phe Tyr Thr Asp Glu Leu Glu Ala Val Leu Val Ala
1               5                   10                  15

Lys Ser Asp Val Leu Val Asp Ala Leu Ala Ala Gly Pro Leu Ala Ala
                20                  25                  30

Asn Leu Lys Ser Pro Ile Leu Ile Thr Pro Lys Thr Tyr Val Ser Ala
            35                  40                  45

Tyr His Lys Glu Asn Leu Glu Ala Lys Ser Ala Asn Lys Val Tyr Lys
        50                  55                  60

Ile Gly Gly Gly Leu Thr Ser Lys Val Met Ser Ser Ile Ala Ser Ser
65                  70                  75                  80

Leu Ser Lys His Asn Thr Thr Pro Thr Glu Pro Gly Asn Ser Gly Gly
                85                  90                  95

Lys Thr Val Met Ile Asp Pro Gly His Gly Ser Asp Thr Gly Thr
                100                 105                 110

Thr Gly Lys Pro Leu Gly Gly Ile Arg Glu Lys Asp Tyr Thr Phe Lys
        115                 120                 125

Tyr Phe Thr Cys Asn Asn
        130
```

```
<210> SEQ ID NO 10
<211> LENGTH: 144
<212> TYPE: PRT
<213> ORGANISM: Clostridium difficile

<400> SEQUENCE: 10
```

```
Asp Val Leu Val Asp Ala Leu Ala Ala Gly Pro Leu Ala Ala Asn Leu
1               5                   10                  15

Lys Ser Pro Ile Leu Ile Thr Pro Lys Thr Tyr Val Ser Ala Tyr His
                20                  25                  30
```

```
Lys Asp Asn Leu Glu Ala Lys Ser Ala Asn Lys Val Tyr Lys Ile Gly
             35                  40                  45

Gly Gly Leu Thr Ser Lys Val Met Ser Ser Ile Ala Ser Ser Leu Ser
 50                  55                  60

Lys His Asn Thr Thr Pro Thr Glu Pro Gly Asn Ser Gly Gly Lys Thr
 65                  70                  75                  80

Val Met Ile Asp Pro Gly His Gly Gly Ser Ala Pro Gly Asn Ser Ser
                 85                  90                  95

Gly Gly Met Ile Glu Lys Asp Tyr Asn Leu Asn Thr Ser Leu Ala Thr
            100                 105                 110

Thr Glu Tyr Leu Arg Ser Lys Gly Phe Asn Val Ile Met Thr Arg Asp
        115                 120                 125

Thr Asp Lys Thr Tyr Leu Leu Glu Ile Glu Leu Leu Tyr Leu Ile His
130                 135                 140
```

<210> SEQ ID NO 11
<211> LENGTH: 601
<212> TYPE: PRT
<213> ORGANISM: Clostridium difficile

<400> SEQUENCE: 11

```
Met Cys Tyr Asp Met Pro Leu Glu Ala Thr Leu Asn Tyr Asn Glu Lys
 1               5                  10                  15

Thr Asp Ser Tyr Glu Gly Val Ile Asn Tyr Asn Lys Asp Pro Glu Tyr
             20                  25                  30

Leu Asn Val Trp Glu Leu Gln Ser Ile Lys Ile Asn Gly Lys Asp Glu
         35                  40                  45

Gln Lys Val Leu Asn Lys Glu Asp Leu Glu Ser Met Gly Leu Asn Leu
 50                  55                  60

Lys Asp Tyr Asp Val Thr Gln Glu Phe Ile Ile Ser Asp Ala Asn Ser
 65                  70                  75                  80

Thr Lys Ala Val Asn Glu Tyr Met Arg Lys Thr Ser Ala Pro Val Lys
                 85                  90                  95

Lys Leu Ala Gly Ala Thr Arg Phe Glu Thr Ala Val Glu Ile Ser Lys
            100                 105                 110

Gln Gly Trp Lys Asp Gly Ser Ser Lys Val Val Ile Val Asn Gly Glu
        115                 120                 125

Leu Ala Ala Asp Gly Ile Thr Ala Thr Pro Leu Ala Ser Thr Tyr Asp
    130                 135                 140

Ala Pro Ile Leu Leu Ala Asn Lys Asp Asp Ile Pro Glu Ser Thr Lys
145                 150                 155                 160

Ala Glu Leu Lys Arg Leu Asn Pro Ser Asp Val Ile Ile Gly Asp
                165                 170                 175

Asp Gly Ser Val Ser Gln Lys Ala Val Ser Gln Ile Lys Ser Ala Val
            180                 185                 190

Asn Val Asn Val Thr Arg Ile Gly Gly Val Asp Arg His Glu Thr Ser
        195                 200                 205

Leu Leu Ile Ala Lys Glu Ile Asp Lys Tyr His Asp Val Asn Lys Ile
    210                 215                 220

Tyr Ile Ala Asn Gly Tyr Ala Gly Glu Tyr Asp Ala Leu Asn Ile Ser
225                 230                 235                 240

Ser Lys Ala Gly Glu Asp Gln Pro Ile Ile Leu Ala Asn Lys Asp
                245                 250                 255

Ser Val Pro Gln Gly Thr Tyr Asn Trp Leu Ser Ser Gln Gly Leu Glu
            260                 265                 270
```

Glu Ala Tyr Tyr Ile Gly Gly Ser Gln Ser Leu Ser Ser Lys Ile Ile
              275                 280                 285

Asp Gln Ile Ser Lys Ile Ala Lys Asn Gly Thr Ser Lys Asn Arg Val
        290                 295                 300

Ser Gly Ala Asp Arg His Glu Thr Asn Ala Asn Val Ile Lys Thr Phe
305                 310                 315                 320

Tyr Pro Asp Lys Glu Leu Ser Ala Met Leu Val Ala Lys Ser Asp Ile
                325                 330                 335

Ile Val Asp Ser Ile Thr Ala Gly Pro Leu Ala Ala Lys Leu Lys Ala
                340                 345                 350

Pro Ile Leu Ile Thr Pro Lys Thr Tyr Val Ser Ala Tyr His Asn Thr
                355                 360                 365

Asn Leu Ser Glu Lys Thr Ala Glu Thr Val Tyr Gln Ile Gly Asp Gly
        370                 375                 380

Met Lys Asp Ser Val Ile Asn Ser Ile Ala Ser Ser Leu Ser Lys His
385                 390                 395                 400

Asn Ala Pro Thr Glu Pro Asp Asn Ser Gly Ser Ala Ala Gly Lys Thr
                405                 410                 415

Val Val Ile Asp Pro Gly His Gly Gly Ser Asp Ser Gly Ala Thr Ser
                420                 425                 430

Gly Leu Asn Gly Gly Ala Gln Glu Lys Lys Tyr Thr Leu Asn Thr Ala
        435                 440                 445

Leu Ala Thr Thr Glu Tyr Leu Arg Ser Lys Gly Ile Asn Val Val Met
        450                 455                 460

Thr Arg Asp Thr Asp Lys Thr Met Ala Leu Gly Glu Arg Thr Ala Leu
465                 470                 475                 480

Ser Asn Thr Ile Lys Pro Asp Leu Phe Thr Ser Ile His Tyr Asn Ala
                485                 490                 495

Ser Asn Gly Ala Gly Asn Gly Val Glu Ile Tyr Tyr Lys Val Lys Asp
            500                 505                 510

Lys Asn Gly Gly Thr Thr Lys Thr Ala Ala Ser Asn Ile Leu Lys Arg
        515                 520                 525

Ile Leu Glu Lys Phe Asn Met Lys Asn Arg Gly Ile Lys Thr Arg Thr
        530                 535                 540

Leu Asp Asn Gly Lys Asp Tyr Leu Tyr Val Leu Arg Thr Asn Asn Tyr
545                 550                 555                 560

Pro Ala Val Leu Val Glu Cys Ala Phe Ile Asp Asn Lys Ser Asp Met
                565                 570                 575

Asp Lys Leu Asn Thr Ala Glu Lys Val Lys Thr Met Gly Thr Gln Ile
                580                 585                 590

Gly Ile Gly Ile Glu Asp Thr Val Lys
        595                 600

<210> SEQ ID NO 12
<211> LENGTH: 206
<212> TYPE: PRT
<213> ORGANISM: Clostridium difficile

<400> SEQUENCE: 12

Met Ile Ser Thr Asn Val Ile Asn Lys Val Asn Glu Ile Thr Lys Asp
1               5                   10                  15

Ser Val Thr Asn Asn Arg Val Tyr Gly Ala Asp Arg His Glu Thr Asn
            20                  25                  30

Ala Asn Val Ile Lys Lys Phe Tyr Thr Asp Asp Glu Leu Glu Ala Val

```
            35                  40                  45
Leu Val Ala Lys Ser Asp Val Leu Val Asp Ala Leu Ala Ala Gly Pro
 50                  55                  60

Leu Ala Ala Asn Leu Lys Ser Pro Ile Leu Ile Thr Pro Lys Thr Tyr
 65                  70                  75                  80

Val Ser Ala Tyr His Lys Asp Asn Leu Glu Ala Lys Ser Ala Asn Lys
                     85                  90                  95

Val Tyr Lys Ile Gly Gly Leu Thr Ser Lys Val Met Ser Ser Ile
                100                 105                 110

Ala Ser Ser Leu Ser Lys His Asn Thr Thr Pro Thr Glu Pro Gly Asn
                115                 120                 125

Ser Gly Gly Lys Thr Val Met Ile Asp Pro Gly His Gly Gly Ser Ala
130                 135                 140

Pro Gly Asn Ser Ser Gly Gly Met Ile Glu Lys Asp Tyr Asn Leu Asn
145                 150                 155                 160

Thr Ser Leu Ala Thr Thr Glu Tyr Leu Arg Ser Lys Gly Phe Asn Val
                165                 170                 175

Ile Met Thr Arg Asp Thr Asp Lys Thr Leu Ser Leu Gly Asn Arg Thr
                180                 185                 190

Ala Tyr Leu Ile Leu Arg Pro Asp Leu Phe Thr Val Tyr Ile
                195                 200                 205

<210> SEQ ID NO 13
<211> LENGTH: 273
<212> TYPE: PRT
<213> ORGANISM: Clostridium difficile

<400> SEQUENCE: 13

Met Leu Val Ala Lys Ser Asp Ile Ile Val Asp Ser Ile Thr Ala Gly
  1               5                  10                  15

Pro Leu Ala Ala Lys Leu Lys Ala Pro Ile Leu Ile Thr Pro Lys Thr
                 20                  25                  30

Tyr Val Ser Ala Tyr His Asn Thr Asn Leu Ser Glu Lys Thr Ala Glu
                 35                  40                  45

Thr Val Tyr Gln Ile Gly Asp Gly Met Lys Asp Ser Val Ile Asn Ser
 50                  55                  60

Ile Ala Ser Ser Leu Ser Lys His Asn Ala Pro Thr Glu Pro Asp Asn
 65                  70                  75                  80

Ser Gly Ser Ala Ala Gly Lys Thr Val Val Ile Asp Pro Gly His Gly
                 85                  90                  95

Gly Ser Asp Ser Gly Ala Thr Ser Gly Leu Asn Gly Gly Ala Gln Glu
                100                 105                 110

Lys Lys Tyr Thr Leu Asn Thr Ala Leu Ala Thr Thr Glu Tyr Leu Arg
                115                 120                 125

Ser Lys Gly Ile Asn Val Val Met Thr Arg Asp Thr Asp Lys Thr Met
130                 135                 140

Ala Leu Gly Glu Arg Thr Ala Leu Ser Asn Thr Ile Lys Pro Asp Leu
145                 150                 155                 160

Phe Thr Ser Ile His Tyr Asn Ala Ser Asn Gly Ala Gly Asn Gly Val
                165                 170                 175

Glu Ile Tyr Tyr Lys Val Lys Asp Lys Asn Gly Gly Thr Thr Lys Thr
                180                 185                 190

Ala Ala Ser Asn Ile Leu Lys Arg Ile Leu Glu Lys Phe Asn Met Lys
                195                 200                 205
```

```
Asn Arg Gly Ile Lys Thr Arg Thr Leu Asp Asn Gly Lys Asp Tyr Leu
    210                 215                 220
Tyr Val Leu Arg Asn Asn Asn Tyr Pro Ala Ile Leu Val Glu Cys Ala
225                 230                 235                 240
Phe Ile Asp Asn Lys Ser Asp Met Asp Lys Leu Asn Thr Ala Glu Lys
                245                 250                 255
Val Lys Thr Met Gly Thr Gln Ile Gly Ile Gly Ile Glu Asp Thr Val
                260                 265                 270
Lys
```

<210> SEQ ID NO 14
<211> LENGTH: 374
<212> TYPE: PRT
<213> ORGANISM: Clostridium difficile

<400> SEQUENCE: 14

```
Asn Ala Asn Gly Gly Glu Val Asp Ala Leu Thr Ile Ala Ala Lys Ala
1               5                   10                  15
Gly Gln Asp Lys Gln Pro Ile Ile Leu Thr Asp Lys Asn Ser Ile Thr
                20                  25                  30
Asp Asn Thr Tyr Lys Trp Leu Lys Ser Glu Asp Leu Gln Asn Ala Tyr
            35                  40                  45
Phe Ile Gly Gly Pro Gln Met Ile Ser Thr Asn Val Ile Asn Lys Val
50                  55                  60
Asn Asp Ile Thr Lys Asp Asn Val Thr Asn Asn Arg Val Tyr Gly Ala
65                  70                  75                  80
Asp Arg His Glu Thr Asn Ala Asn Val Ile Lys Lys Phe Tyr Thr Asp
                85                  90                  95
Asp Glu Leu Glu Ala Val Leu Val Ala Lys Ser Asp Val Leu Val Asp
            100                 105                 110
Ala Leu Ala Ala Gly Pro Leu Ala Ala Asn Leu Lys Ser Pro Ile Leu
        115                 120                 125
Ile Thr Pro Lys Thr Tyr Val Ser Ala Tyr His Lys Asp Asn Leu Glu
130                 135                 140
Ala Lys Ser Ala Asn Lys Val Tyr Lys Ile Gly Gly Gly Leu Thr Ser
145                 150                 155                 160
Lys Val Met Asn Ser Ile Ala Ser Ser Leu Ser Lys His Asn Thr Thr
                165                 170                 175
Pro Thr Glu Pro Gly Asn Ser Gly Gly Lys Thr Val Met Ile Asp Pro
            180                 185                 190
Gly His Gly Gly Ser Asp Thr Gly Thr Thr Gly Lys Pro Leu Gly Gly
        195                 200                 205
Ile Lys Glu Lys Asp Tyr Thr Leu Asn Thr Ser Leu Ala Thr Thr Glu
210                 215                 220
Tyr Leu Arg Ser Lys Gly Phe Asn Val Ile Met Thr Arg Asp Thr Asp
225                 230                 235                 240
Lys Thr Leu Ser Leu Gly Asn Arg Thr Ala Leu Ser Asn Ser Leu Arg
                245                 250                 255
Pro Asp Leu Phe Thr Ser Ile His Tyr Asn Ala Ser Asp Thr Thr Gly
            260                 265                 270
Asn Gly Val Glu Val Phe Tyr Lys Leu Lys Asp Lys Asp Gly Gly Thr
        275                 280                 285
Thr Lys Thr Val Ala Thr Asn Ile Leu Asn Arg Ile Leu Glu Lys Phe
290                 295                 300
```

```
Asn Leu Lys Asn Arg Gly Ala Lys Thr Arg Thr Leu Ser Thr Asp Pro
305                 310                 315                 320

Thr Lys Asp Tyr Leu Tyr Val Leu Arg Asn Asn Asp Met Pro Ala Val
            325                 330                 335

Leu Val Glu Cys Ala Phe Leu Asp Asn Glu Lys Asp Met Ser Leu Leu
        340                 345                 350

Asn Thr Ser Asn Lys Val Lys Glu Met Gly Thr Gln Ile Gly Lys Gly
    355                 360                 365

Ile Glu Asp Ser Leu Lys
    370

<210> SEQ ID NO 15
<211> LENGTH: 178
<212> TYPE: PRT
<213> ORGANISM: Clostridium difficile

<400> SEQUENCE: 15

Met Ile Ser Thr Asn Val Ile Asn Lys Val Asn Asp Ile Thr Lys Asp
1               5                   10                  15

Asn Val Thr Asn Asn Arg Val Tyr Gly Ala Asp Arg His Glu Thr Asn
            20                  25                  30

Ala Asn Val Ile Lys Lys Phe Tyr Thr Asp Asp Glu Leu Glu Ala Val
        35                  40                  45

Leu Val Ala Lys Ser Asp Val Leu Val Asp Ala Leu Ala Ala Gly Pro
    50                  55                  60

Leu Ala Ala Asn Leu Lys Ser Pro Ile Leu Ile Thr Pro Lys Thr Tyr
65                  70                  75                  80

Val Ser Ala Tyr His Lys Asp Asn Leu Glu Ala Lys Ser Ala Asn Lys
                85                  90                  95

Val Tyr Lys Ile Gly Gly Gly Leu Thr Ser Lys Val Met Ser Ser Ile
            100                 105                 110

Ala Ser Ser Leu Ser Lys His Asn Thr Thr Pro Thr Glu Pro Gly Asn
        115                 120                 125

Ser Gly Gly Lys Thr Val Met Ile Asp Pro Gly His Gly Gly Ser Asp
    130                 135                 140

Thr Gly Thr Thr Gly Lys Pro Leu Gly Gly Ile Lys Glu Lys Asp Tyr
145                 150                 155                 160

Thr Leu Asn Thr Ser Leu Ala Thr Thr Glu Tyr Leu Arg Ser Arg Asp
                165                 170                 175

Ser Met

<210> SEQ ID NO 16
<211> LENGTH: 114
<212> TYPE: PRT
<213> ORGANISM: Clostridium difficile

<400> SEQUENCE: 16

Leu Val Asp Ala Leu Ala Ala Gly Pro Leu Ala Ala Asn Leu Lys Ser
1               5                   10                  15

Pro Ile Leu Ile Thr Pro Lys Thr Tyr Val Ser Ala Tyr His Lys Glu
            20                  25                  30

Asn Leu Glu Ala Lys Ser Ala Asn Lys Val Tyr Lys Ile Gly Gly Gly
        35                  40                  45

Leu Thr Ser Lys Val Met Ser Ser Ile Ala Ser Ser Leu Ser Lys His
    50                  55                  60

Asn Thr Thr Pro Thr Glu Pro Gly Asn Ser Gly Gly Lys Thr Val Met
```

```
                65                  70                  75                  80
Ile Asp Pro Gly His Gly Gly Ser Asp Thr Gly Thr Thr Gly Lys Pro
                    85                  90                  95
Leu Gly Gly Ile Lys Glu Lys Asp Tyr Thr Phe Lys Tyr Phe Thr Cys
                    100                 105                 110
Asn Asn

<210> SEQ ID NO 17
<211> LENGTH: 582
<212> TYPE: PRT
<213> ORGANISM: Clostridium difficile

<400> SEQUENCE: 17

Met Lys Lys Thr Thr Lys Leu Leu Ala Thr Gly Met Leu Ser Val Ala
1               5                   10                  15

Met Val Ala Pro Asn Val Ala Leu Ala Ala Glu Asn Thr Thr Ala Asn
                20                  25                  30

Thr Glu Ser Asn Ser Asp Ile Asn Ile Asn Leu Gln Arg Lys Ser Val
            35                  40                  45

Val Leu Gly Ser Lys Ser Asn Ala Ser Val Lys Phe Lys Glu Lys Leu
        50                  55                  60

Asn Ala Asp Ser Ile Thr Leu Asn Phe Met Cys Tyr Asp Met Pro Leu
65                  70                  75                  80

Glu Ala Thr Leu Asn Tyr Asn Glu Lys Thr Asp Ser Tyr Glu Gly Val
                85                  90                  95

Ile Asn Tyr Asn Lys Asp Pro Glu Tyr Leu Asn Val Trp Glu Leu Gln
                100                 105                 110

Ser Ile Lys Ile Asn Gly Lys Asp Glu Gln Lys Val Leu Asn Lys Glu
            115                 120                 125

Asp Leu Glu Ser Met Gly Leu Asn Leu Lys Asp Tyr Asp Val Thr Gln
        130                 135                 140

Glu Phe Ile Ile Ser Asp Ala Asn Ser Thr Lys Ala Val Asn Glu Tyr
145                 150                 155                 160

Met Arg Lys Thr Ser Ala Pro Val Lys Lys Leu Ala Gly Ala Thr Arg
                165                 170                 175

Phe Glu Thr Ala Val Glu Ile Ser Lys Gln Gly Trp Lys Asp Gly Ser
                180                 185                 190

Ser Lys Val Val Ile Val Asn Gly Glu Leu Ala Ala Asp Gly Ile Thr
            195                 200                 205

Ala Thr Pro Leu Ala Ser Thr Tyr Asp Ala Pro Ile Leu Leu Ala Asn
        210                 215                 220

Lys Asp Asp Ile Pro Glu Ser Thr Lys Ala Glu Leu Lys Arg Leu Asn
225                 230                 235                 240

Pro Ser Asp Val Ile Ile Gly Asp Asp Gly Ser Val Ser Gln Lys
                245                 250                 255

Ala Val Ser Gln Ile Lys Ser Ala Val Asn Val Asn Val Thr Arg Ile
                260                 265                 270

Gly Gly Val Asp Arg His Glu Thr Ser Leu Leu Ile Ala Lys Glu Ile
            275                 280                 285

Asp Lys Tyr His Asp Val Asn Lys Ile Tyr Ile Ala Asn Gly Tyr Ala
        290                 295                 300

Gly Glu Tyr Asp Ala Leu Asn Ile Ser Ser Lys Ala Gly Glu Asp Gln
305                 310                 315                 320

Gln Pro Ile Ile Leu Ala Asn Lys Asp Ser Val Pro Gln Gly Thr Tyr
```

```
                        325                 330                 335
Asn Trp Leu Ser Ser Gln Gly Leu Glu Glu Ala Tyr Tyr Ile Gly Gly
                340                 345                 350

Ser Gln Ser Leu Ser Ser Lys Leu Ile Asp Gln Ile Ser Lys Ile Ala
            355                 360                 365

Lys Asn Gly Thr Ser Lys Asn Arg Val Ser Gly Ala Asp Arg His Glu
        370                 375                 380

Thr Asn Ala Asn Val Ile Lys Thr Phe Tyr Pro Asp Lys Glu Leu Ser
385                 390                 395                 400

Ala Met Leu Val Ala Lys Ser Asp Ile Ile Val Asp Ser Ile Thr Ala
                405                 410                 415

Gly Pro Leu Ala Ala Lys Leu Lys Ala Pro Ile Leu Ile Thr Pro Lys
                420                 425                 430

Thr Tyr Val Ser Ala Tyr His Ser Thr Asn Leu Ser Glu Lys Thr Ala
                435                 440                 445

Glu Thr Val Tyr Gln Ile Gly Asp Gly Met Lys Asp Ser Val Ile Asn
                450                 455                 460

Ser Ile Ala Ser Ser Leu Ser Lys His Asn Ala Pro Thr Glu Pro Asp
465                 470                 475                 480

Asn Ser Gly Ser Ala Ala Gly Lys Thr Val Val Ile Asp Pro Gly His
                485                 490                 495

Gly Gly Ser Asp Ser Gly Ala Thr Ser Gly Leu Asn Gly Gly Ala Gln
                500                 505                 510

Glu Lys Lys Tyr Thr Leu Asn Thr Ala Leu Ala Thr Thr Glu Tyr Leu
                515                 520                 525

Arg Ser Lys Gly Ile Asn Val Val Met Thr Arg Asp Thr Asp Lys Thr
                530                 535                 540

Met Ala Leu Gly Glu Arg Thr Ala Leu Ser Asn Thr Ile Lys Pro Asp
545                 550                 555                 560

Leu Phe Thr Ser Ile His Tyr Asn Ala Ser Asn Gly Ala Gly Asn Gly
                565                 570                 575

Val Glu Ile Ile Thr Lys
                580

<210> SEQ ID NO 18
<211> LENGTH: 469
<212> TYPE: PRT
<213> ORGANISM: Clostridium difficile

<400> SEQUENCE: 18

Gly Ile Ile Ser Thr Pro Leu Ala Thr Thr Tyr Asn Ala Pro Ile Leu
1               5                   10                  15

Leu Val Glu Lys Asn Asn Val Pro Asn Ser Val Lys Ser Glu Leu Lys
                20                  25                  30

Arg Leu Asn Pro Lys Asp Ile Ile Ile Gly Asp Glu Asn Ala Ile
            35                  40                  45

Ser Lys Thr Thr Ala Asn Gln Ile Lys Ser Thr Val Asn Ala Ser Gln
        50                  55                  60

Thr Arg Leu Asn Gly Ser Asn Arg Tyr Glu Thr Ser Leu Leu Ile Ala
65                  70                  75                  80

Lys Glu Ile Asp Lys Asn His Asp Val Glu Lys Val Tyr Ile Thr Asn
                85                  90                  95

Ala Asn Gly Gly Glu Val Asp Ala Leu Thr Ile Ala Ala Lys Ala Gly
                100                 105                 110
```

-continued

```
Gln Asp Lys Gln Pro Ile Ile Leu Thr Asp Lys Asp Ser Ile Thr Asp
        115                 120                 125
Asn Thr Tyr Lys Trp Leu Lys Ser Glu Asp Leu Gln Asn Ala Tyr Phe
    130                 135                 140
Ile Gly Gly Pro Gln Met Ile Ser Thr Asn Val Ile Asn Lys Val Asn
145                 150                 155                 160
Gly Ile Thr Lys Asp Ser Val Thr Asn Asn Arg Val Tyr Gly Ala Asp
                165                 170                 175
Arg His Glu Thr Asn Ala Asn Val Ile Lys Lys Phe Tyr Thr Asp Asp
            180                 185                 190
Glu Leu Glu Ala Val Leu Val Ala Lys Ser Asp Val Leu Val Asp Ala
        195                 200                 205
Leu Ala Ala Gly Pro Leu Ala Ala Asn Leu Lys Ser Pro Ile Leu Ile
        210                 215                 220
Thr Pro Lys Thr Tyr Val Ser Ala Tyr His Lys Glu Asn Leu Glu Ala
225                 230                 235                 240
Lys Ser Ala Asn Lys Val Tyr Lys Ile Gly Gly Leu Thr Ser Lys
                245                 250                 255
Val Met Ser Ser Ile Ala Ser Ser Leu Ser Lys His Asn Thr Thr Pro
                260                 265                 270
Thr Glu Pro Gly Asn Ser Gly Gly Lys Thr Val Met Ile Asp Pro Gly
            275                 280                 285
His Gly Gly Ser Asp Thr Gly Thr Thr Gly Lys Pro Leu Gly Gly Ile
        290                 295                 300
Arg Glu Lys Asp Tyr Thr Leu Asn Thr Ser Leu Ala Thr Thr Glu Tyr
305                 310                 315                 320
Leu Arg Ser Lys Gly Phe Asn Val Ile Met Thr Arg Asp Thr Asp Lys
                325                 330                 335
Thr Leu Ser Leu Gly Asn Arg Thr Ala Leu Ser Asn Ser Leu Arg Pro
            340                 345                 350
Asp Leu Phe Thr Ser Ile His Tyr Asn Ala Ser Asp Thr Thr Gly Asn
        355                 360                 365
Gly Val Glu Val Phe Tyr Lys Leu Lys Asp Lys Asp Gly Gly Thr Thr
    370                 375                 380
Lys Thr Val Ala Thr Asn Ile Leu Asn Arg Ile Leu Glu Lys Phe Asn
385                 390                 395                 400
Leu Lys Asn Arg Gly Ala Lys Thr Arg Thr Leu Ser Thr Asp Pro Thr
                405                 410                 415
Lys Asp Tyr Leu Tyr Val Leu Arg Asn Asn Asp Met Pro Ala Val Leu
            420                 425                 430
Val Glu Cys Ala Phe Leu Asp Asn Glu Lys Asp Met Ser Leu Leu Asn
        435                 440                 445
Thr Ser Asn Lys Val Lys Glu Met Gly Thr Gln Ile Gly Lys Gly Ile
    450                 455                 460
Glu Asp Ser Leu Lys
465

<210> SEQ ID NO 19
<211> LENGTH: 267
<212> TYPE: PRT
<213> ORGANISM: Clostridium difficile

<400> SEQUENCE: 19

Met Gln Thr Tyr Ala Ile Asp Ala Leu Ala Ala Gly Pro Leu Ala Ala
1               5                   10                  15
```

-continued

```
Asn Leu Lys Ser Pro Ile Leu Ile Thr Pro Lys Thr Tyr Val Ser Ala
             20                  25                  30

Tyr His Lys Glu Asn Leu Glu Ala Lys Ser Ala Asn Lys Val Tyr Lys
         35                  40                  45

Ile Gly Gly Gly Leu Thr Ser Lys Val Met Asn Ser Ile Ala Ser Ser
     50                  55                  60

Leu Ser Lys His Asn Thr Thr Pro Thr Glu Pro Gly Asn Ser Gly Gly
 65                  70                  75                  80

Lys Thr Val Met Ile Asp Pro Gly His Gly Ser Ala Pro Gly Asn
                 85                  90                  95

Ser Ser Gly Gly Met Ile Glu Lys Asp Tyr Asn Leu Asn Thr Ser Leu
            100                 105                 110

Ala Thr Thr Glu Tyr Leu Arg Ser Lys Gly Phe Asn Val Ile Met Thr
        115                 120                 125

Arg Asp Thr Asp Lys Thr Leu Ser Leu Gly Asn Arg Thr Ala Leu Ser
130                 135                 140

Asn Ser Leu Lys Pro Asp Leu Phe Thr Ser Ile His Tyr Asn Gly Ser
145                 150                 155                 160

Thr Asn Lys Gln Gly His Gly Val Glu Val Phe Tyr Lys Leu Lys Asp
                165                 170                 175

Lys Asn Gly Gly Thr Thr Lys Thr Val Ala Thr Asn Ile Leu Asn Arg
            180                 185                 190

Ile Leu Glu Lys Phe Lys Leu Thr Asn Arg Gly Ile Lys Thr Arg Val
        195                 200                 205

Leu Pro Ser Asp Ser Thr Lys Asp Tyr Leu Tyr Val Leu Arg Ser Asn
    210                 215                 220

Asp Met Pro Ala Val Leu Val Glu Cys Ala Phe Leu Asp Asn Glu Asn
225                 230                 235                 240

Asp Met Ser Leu Ile Asn Ser Ser Ala Lys Val Lys Glu Met Gly Thr
                245                 250                 255

Gln Ile Gly Lys Gly Ile Glu Asp Ser Leu Lys
            260                 265
```

<210> SEQ ID NO 20
<211> LENGTH: 603
<212> TYPE: PRT
<213> ORGANISM: Clostridium difficile

<400> SEQUENCE: 20

```
Lys Tyr Lys Cys Tyr Asp Met Pro Leu Asp Thr Thr Leu Asn Tyr Asn
 1               5                  10                  15

Gln Ser Thr Glu Ser Tyr Glu Gly Thr Ile Asn Tyr Asn Lys Asp Pro
             20                  25                  30

Glu Tyr Leu Asn Val Trp Glu Leu Gln Gly Ile Thr Ile Asn Ser Lys
         35                  40                  45

Asn Asn Pro Lys Thr Leu Asn Lys Gln Glu Leu Glu Lys Met Gly Leu
     50                  55                  60

Asn Leu Lys Asp Tyr Asn Val Thr Gln Glu Cys Ile Ile Glu Asp Ile
 65                  70                  75                  80

Thr Ser Arg Lys Asp Val Asn Lys Tyr Leu Arg Lys Thr Ser Ala Pro
                 85                  90                  95

Ile Thr Glu Leu Thr Gly Ser Asp Arg Tyr Glu Thr Ala Val Lys Ile
            100                 105                 110

Ser Lys Glu Gly Trp Lys Asn Gly Ser Asp Lys Val Val Ile Ile Asn
```

```
            115                 120                 125
Gly Asp Val Ser Ile Asp Gly Ile Ile Ser Thr Pro Leu Ala Thr Thr
            130                 135                 140
Tyr Asn Ala Pro Ile Leu Leu Val Glu Lys Asn Asn Val Pro Asn Ser
145                 150                 155                 160
Val Lys Ser Glu Leu Lys Arg Leu Asn Pro Arg Asp Val Ile Ile Ile
                165                 170                 175
Gly Asp Glu Asn Ala Ile Ser Lys Thr Thr Ala Asn Gln Ile Lys Ser
            180                 185                 190
Thr Val Asn Ala Ser Gln Thr Arg Leu Lys Gly Ser Asn Arg Tyr Glu
            195                 200                 205
Thr Ser Leu Leu Ile Ala Lys Glu Ile Asp Lys Asn His Asp Val Glu
            210                 215                 220
Lys Val Tyr Ile Thr Asn Ala Asn Gly Gly Val Asp Ala Leu Thr
225                 230                 235                 240
Ile Ala Ala Lys Ala Gly Gln Asp Lys Gln Pro Ile Ile Leu Thr Asp
                245                 250                 255
Lys Asp Ser Ile Thr Asp Asn Thr Tyr Lys Trp Leu Lys Ser Glu Asp
            260                 265                 270
Leu Gln Asn Ala Tyr Phe Ile Gly Gly Pro Gln Met Ile Ser Thr Asn
            275                 280                 285
Val Ile Asn Lys Val Asn Asp Ile Thr Lys Asp Asn Val Thr Asn Asn
            290                 295                 300
Arg Val Tyr Gly Ala Asp Arg His Glu Thr Asn Ala Asn Val Ile Lys
305                 310                 315                 320
Lys Phe Tyr Thr Asp Asp Glu Leu Glu Ala Val Leu Ala Lys Ser
                325                 330                 335
Asp Val Leu Val Asp Ala Leu Ala Ala Gly Pro Leu Ala Ala Asn Leu
            340                 345                 350
Lys Ser Pro Ile Leu Ile Thr Pro Lys Thr Tyr Val Ser Ala Tyr His
            355                 360                 365
Lys Asp Asn Leu Glu Ala Lys Ser Ala Asn Lys Val Tyr Lys Ile Gly
            370                 375                 380
Gly Gly Leu Thr Ser Lys Val Met Ser Ser Ile Ala Ser Ser Leu Ser
385                 390                 395                 400
Lys His Asn Thr Thr Pro Thr Glu Pro Gly Asn Ser Gly Gly Lys Thr
                405                 410                 415
Val Met Ile Asp Pro Gly His Gly Gly Ser Asp Thr Gly Thr Thr Gly
                420                 425                 430
Lys Pro Leu Gly Gly Ile Arg Glu Lys Asp Tyr Thr Leu Asn Thr Ser
            435                 440                 445
Leu Ala Thr Thr Glu Tyr Leu Arg Ser Lys Gly Phe Asn Val Ile Met
            450                 455                 460
Thr Arg Asp Thr Asp Lys Thr Leu Ser Leu Gly Asn Arg Thr Ala Leu
465                 470                 475                 480
Ser Asn Ser Leu Arg Pro Asp Leu Phe Thr Ser Ile His Tyr Asn Ala
                485                 490                 495
Ser Asp Thr Thr Gly Asn Gly Val Glu Val Phe Tyr Lys Leu Lys Asp
            500                 505                 510
Lys Asp Gly Gly Thr Thr Lys Thr Val Ala Thr Asn Ile Leu Asn Arg
            515                 520                 525
Ile Leu Glu Lys Phe Asn Leu Lys Asn Arg Gly Ala Lys Thr Arg Thr
            530                 535                 540
```

Leu Ser Thr Asp Pro Thr Lys Asp Tyr Leu Tyr Val Leu Arg Asn Asn
545                 550                 555                 560

Asp Met Pro Ala Val Leu Val Glu Cys Ala Phe Leu Asp Asn Glu Lys
                565                 570                 575

Asp Met Ser Leu Leu Asn Thr Ser Asn Lys Val Lys Glu Met Gly Thr
            580                 585                 590

Gln Ile Gly Lys Gly Ile Glu Asp Ser Leu Lys
        595                 600

<210> SEQ ID NO 21
<211> LENGTH: 416
<212> TYPE: PRT
<213> ORGANISM: Clostridium difficile

<400> SEQUENCE: 21

Asn Gln Ile Lys Ser Thr Val Asn Ala Ser Gln Thr Arg Leu Asn Gly
1               5                   10                  15

Ser Asn Arg Tyr Glu Thr Ser Leu Leu Ile Ala Lys Glu Ile Asp Lys
            20                  25                  30

Asn His Asp Val Glu Lys Val Tyr Ile Thr Asn Ala Asn Gly Gly Glu
        35                  40                  45

Val Asp Ala Leu Thr Ile Ala Ala Lys Ala Gly Gln Asp Lys Gln Pro
    50                  55                  60

Ile Ile Leu Thr Asp Lys Asp Ser Ile Thr Asp Asn Thr Tyr Lys Trp
65                  70                  75                  80

Leu Lys Ser Glu Asp Leu Gln Asn Ala Tyr Phe Ile Gly Gly Pro Gln
                85                  90                  95

Met Ile Ser Thr Asn Val Ile Asn Lys Val Asn Asp Ile Thr Lys Asp
            100                 105                 110

Asn Val Thr Asn Asn Arg Val Tyr Gly Ala Asp Arg His Glu Thr Asn
        115                 120                 125

Ala Asn Val Ile Lys Lys Phe Tyr Thr Asp Asp Glu Leu Glu Ala Val
    130                 135                 140

Leu Val Ala Lys Ser Asp Val Leu Val Asp Ala Leu Ala Ala Gly Pro
145                 150                 155                 160

Leu Ala Ala Asn Leu Lys Ser Pro Ile Leu Ile Thr Pro Lys Thr Tyr
                165                 170                 175

Val Ser Ala Tyr His Lys Glu Asn Leu Glu Ala Lys Ser Ala Asn Lys
            180                 185                 190

Val Tyr Lys Ile Gly Gly Gly Leu Thr Ser Lys Val Met Asn Ser Ile
        195                 200                 205

Ala Ser Ser Leu Ser Lys His Asn Thr Thr Pro Thr Glu Pro Gly Asn
    210                 215                 220

Ser Gly Gly Lys Thr Val Met Ile Asp Pro Gly His Gly Gly Ser Asp
225                 230                 235                 240

Thr Gly Thr Thr Gly Lys Pro Leu Gly Gly Ile Lys Glu Lys Asp Tyr
                245                 250                 255

Thr Leu Asn Thr Ser Leu Ala Thr Thr Glu Tyr Leu Arg Ser Lys Gly
            260                 265                 270

Phe Asn Val Ile Met Thr Arg Asp Thr Asp Lys Thr Leu Ser Leu Gly
        275                 280                 285

Asn Arg Thr Ala Leu Ser Asn Ser Leu Arg Pro Asp Leu Phe Thr Ser
    290                 295                 300

Ile His Tyr Asn Ala Ser Asp Thr Thr Gly Asn Gly Val Glu Val Phe

```
            305                 310                 315                 320
Tyr Lys Leu Lys Asp Lys Asp Gly Gly Thr Thr Lys Thr Val Ala Thr
                    325                 330                 335

Asn Ile Leu Asn Arg Ile Leu Glu Lys Phe Asn Leu Lys Asn Arg Gly
                340                 345                 350

Ala Lys Thr Arg Thr Leu Ser Thr Asp Pro Thr Lys Asp Tyr Leu Tyr
            355                 360                 365

Val Leu Arg Asn Asn Asp Met Pro Ala Val Leu Val Glu Cys Ala Phe
        370                 375                 380

Leu Asp Asn Glu Lys Asp Met Ser Leu Leu Asn Thr Ser Asn Lys Val
385                 390                 395                 400

Lys Glu Met Gly Thr Gln Ile Gly Lys Gly Ile Glu Asp Ser Leu Lys
                    405                 410                 415

<210> SEQ ID NO 22
<211> LENGTH: 550
<212> TYPE: PRT
<213> ORGANISM: Clostridium difficile

<400> SEQUENCE: 22

Met Leu Ser Lys Glu Ile Asn Met Arg Arg Asn Thr Lys Leu Leu Thr
1               5                   10                  15

Thr Gly Ile Leu Ser Met Ala Ile Val Thr Pro Thr Met Ala Phe Ala
            20                  25                  30

Thr Glu Ser Asn Ala Met Glu Asn Asn Ala Asp Leu Asn Ile Asn Leu
        35                  40                  45

Glu Lys Lys Ser Ile Val Leu Gly Ser Thr Ser Lys Val Ser Val Lys
    50                  55                  60

Phe Lys Glu Lys Pro Asp Ala Asp Ser Ile Thr Leu Lys Tyr Lys Cys
65                  70                  75                  80

Tyr Asp Met Pro Leu Asp Thr Thr Leu Asn Tyr Asn Gln Ser Thr Glu
                85                  90                  95

Ser Tyr Glu Gly Thr Ile Asn Tyr Asn Lys Asp Pro Glu Tyr Leu Asn
            100                 105                 110

Val Trp Glu Leu Gln Gly Ile Thr Ile Asn Ser Lys Asn Asn Pro Lys
        115                 120                 125

Thr Leu Asn Lys Gln Glu Leu Glu Lys Met Gly Leu Asn Leu Lys Asp
    130                 135                 140

Tyr Asn Val Thr Gln Glu Cys Ile Ile Glu Asp Ile Thr Ser Arg Lys
145                 150                 155                 160

Asp Val Asn Lys Tyr Leu Arg Lys Thr Ser Ala Pro Ile Thr Glu Leu
                165                 170                 175

Thr Gly Ser Asp Arg Tyr Glu Thr Ala Val Lys Ile Ser Lys Glu Gly
            180                 185                 190

Trp Lys Asn Gly Ser Asp Lys Val Val Ile Asn Gly Asp Val Ser
        195                 200                 205

Ile Asp Gly Ile Ile Ser Thr Pro Leu Ala Thr Thr Tyr Asn Ala Pro
    210                 215                 220

Ile Leu Leu Val Glu Lys Asn Asn Val Pro Asn Ser Val Lys Ser Glu
225                 230                 235                 240

Leu Lys Arg Leu Asn Pro Arg Asp Val Ile Ile Gly Asp Glu Asn
                245                 250                 255

Ala Ile Ser Lys Thr Thr Ala Asn Gln Ile Lys Ser Thr Val Asn Ala
            260                 265                 270
```

```
Ser Gln Thr Arg Leu Lys Gly Ser Asn Arg Tyr Glu Thr Ser Leu Leu
            275                 280                 285

Ile Ala Lys Glu Ile Asp Lys Asn His Asp Val Glu Lys Val Tyr Ile
        290                 295                 300

Thr Asn Ala Asn Gly Gly Glu Val Asp Ala Leu Thr Ile Ala Ala Lys
305                 310                 315                 320

Ala Gly Gln Asp Lys Gln Pro Ile Ile Leu Thr Asp Lys Asn Ser Ile
                325                 330                 335

Thr Asp Asn Thr Tyr Lys Trp Leu Lys Ser Glu Asp Leu Gln Asn Ala
            340                 345                 350

Tyr Phe Ile Gly Gly Pro Gln Met Ile Ser Thr Asn Val Ile Asn Lys
        355                 360                 365

Val Asn Asp Ile Thr Lys Asp Asn Val Thr Asn Asn Arg Val Tyr Gly
    370                 375                 380

Ala Asp Arg His Glu Thr Asn Ala Asn Val Ile Lys Lys Phe Tyr Thr
385                 390                 395                 400

Asp Asp Glu Leu Glu Ala Val Leu Val Ala Lys Ser Asp Val Leu Val
                405                 410                 415

Asp Ala Leu Ala Ala Gly Pro Leu Ala Ala Asn Leu Lys Ser Pro Ile
            420                 425                 430

Leu Ile Thr Pro Lys Thr Tyr Val Ser Ala Tyr His Lys Asp Asn Leu
        435                 440                 445

Glu Ala Lys Ser Ala Asn Lys Val Tyr Lys Ile Gly Gly Gly Leu Thr
    450                 455                 460

Ser Lys Val Met Ser Ser Ile Ala Ser Ser Leu Ser Lys His Asn Thr
465                 470                 475                 480

Thr Pro Thr Glu Pro Gly Asn Ser Gly Gly Lys Thr Val Met Ile Asp
                485                 490                 495

Pro Gly His Gly Gly Ser Ala Pro Gly Asn Ser Ser Gly Gly Met Ile
            500                 505                 510

Glu Lys Asp Tyr Asn Leu Asn Thr Ser Leu Ala Thr Thr Glu Tyr Leu
        515                 520                 525

Arg Ser Lys Gly Phe Asn Val Ile Met Thr Arg Asp Thr Asp Lys Thr
    530                 535                 540

Leu Ser Leu Gly Asn Arg
545                 550

<210> SEQ ID NO 23
<211> LENGTH: 672
<212> TYPE: PRT
<213> ORGANISM: Clostridium difficile

<400> SEQUENCE: 23

Met Arg Arg Asn Gly Lys Leu Leu Thr Thr Gly Ile Leu Ser Met Ala
1               5                   10                  15

Ile Val Ala Pro Thr Met Ala Phe Ala Thr Glu Ser Ser Ala Met Glu
            20                  25                  30

Asn Asn Ala Asp Leu Asn Ile Ser Leu Glu Lys Lys Ser Ile Val Leu
        35                  40                  45

Gly Ser Thr Ser Lys Val Ser Val Lys Phe Lys Glu Lys Pro Asp Ala
    50                  55                  60

Asp Ser Ile Thr Leu Lys Tyr Lys Cys Tyr Asp Met Pro Leu Asp Thr
65                  70                  75                  80

Thr Ile Asn Tyr Asn Lys Ser Thr Gly Ala Tyr Glu Gly Thr Ile Asn
                85                  90                  95
```

-continued

Tyr Asn Lys Asp Pro Glu Tyr Gln Asn Val Trp Glu Leu Gln Gly Ile
            100                 105                 110

Ile Ile Asn Ser Glu Asn Asn Pro Lys Thr Leu Asn Lys Gln Asp Leu
        115                 120                 125

Glu Lys Met Gly Leu Asn Leu Lys Asp Tyr Asn Val Thr Gln Glu Cys
130                 135                 140

Ile Ile Glu Asp Ile Thr Ser Arg Lys Asp Val Ser Lys Tyr Leu Arg
145                 150                 155                 160

Lys Thr Ser Ala Pro Ile Thr Glu Leu Thr Gly Ser Asp Arg Tyr Glu
                165                 170                 175

Thr Ala Val Lys Ile Ser Lys Glu Gly Trp Lys Asn Gly Ser Asp Lys
            180                 185                 190

Val Ile Ile Ile Asn Gly Asp Val Ser Ile Asp Gly Ile Ile Ser Thr
        195                 200                 205

Pro Leu Ala Thr Thr Tyr Asn Ala Pro Ile Leu Leu Val Glu Lys Asn
    210                 215                 220

Asn Val Pro Asp Ser Val Lys Ser Glu Leu Lys Arg Leu Asn Pro Lys
225                 230                 235                 240

Asp Val Ile Ile Ile Gly Asp Glu Asn Ser Val Ser Lys Thr Ser Ala
                245                 250                 255

Asn Gln Ile Lys Ser Ala Ala Asn Ala Asn Gln Thr Arg Leu Asn Gly
            260                 265                 270

Ser Asn Arg Tyr Glu Thr Ser Leu Leu Ile Ala Lys Glu Ile Asp Lys
        275                 280                 285

Asn His Asp Val Asp Lys Val Tyr Ile Thr Asn Gly Lys Asp Gly Gly
    290                 295                 300

Glu Ile Asp Ala Leu Thr Ile Ala Ala Lys Ala Gly Gln Asp Lys Gln
305                 310                 315                 320

Pro Ile Ile Val Ala Asp Lys Asp Ser Ile Thr Asn Asn Thr Tyr Gln
                325                 330                 335

Trp Leu Glu Ser Glu Asp Leu Gln Ser Ala Tyr Phe Ile Gly Gly Pro
            340                 345                 350

Gln Met Ile Ser Thr Asn Val Ile Asn Lys Val Asn Asp Ile Thr Lys
        355                 360                 365

Asp Asn Val Thr Asn Asn Arg Val Ser Gly Ala Asp Arg His Glu Thr
    370                 375                 380

Asn Ala Asn Val Ile Lys Lys Phe Tyr Thr Glu Asp Leu Glu Ala
385                 390                 395                 400

Val Leu Val Ala Lys Ser Asp Glu Leu Val Asp Ala Leu Ala Ala Gly
                405                 410                 415

Ser Leu Ala Ala Ser Leu Lys Ser Pro Ile Leu Ile Thr Pro Lys Thr
            420                 425                 430

Tyr Val Ser Ala Tyr His Lys Ala Asn Leu Glu Ala Lys Ser Ala Asn
        435                 440                 445

Lys Val Tyr Lys Ile Gly Gly Gly Leu Thr Ser Lys Val Met Asn Ser
    450                 455                 460

Ile Ala Ala Ser Leu Ser Lys His Asn Thr Thr Pro Thr Asp Pro Gly
465                 470                 475                 480

Asn Asn Thr Gly Ala Lys Thr Val Met Ile Asp Pro Gly His Gly Gly
                485                 490                 495

Ser Ala Pro Gly Asn Ser Phe Gly Gly Met Ile Glu Lys Asp Tyr Asn
            500                 505                 510

```
Leu Asn Thr Ser Leu Ala Thr Thr Glu Tyr Leu Arg Ser Lys Gly Ile
            515                 520                 525

Asn Val Ile Met Thr Arg Asp Ala Asp Lys Thr Val Ser Leu Gly Ser
            530                 535                 540

Arg Thr Ala Leu Ser Asn Ser Leu Lys Pro Asp Leu Phe Thr Ser Ile
545                 550                 555                 560

His Tyr Asn Gly Asp Asn Asn Arg Lys Gly His Gly Val Glu Val Phe
            565                 570                 575

Tyr Lys Leu Lys Asp Lys Asn Gly Gly Thr Thr Lys Thr Val Ala Thr
            580                 585                 590

Asn Ile Leu Asn Arg Ile Leu Glu Lys Phe Lys Leu Thr Asn Arg Gly
            595                 600                 605

Ile Lys Ile Arg Thr Leu Asp Asp Asn Pro Ala Lys Asp Tyr Leu Tyr
            610                 615                 620

Val Leu Arg Thr Asn Asn Val Pro Ala Val Leu Val Glu Cys Ala Phe
625                 630                 635                 640

Leu Asp Asn Ala Ser Asp Met Ser Leu Ile Asn Ser Pro Ala Lys Val
            645                 650                 655

Lys Glu Met Gly Thr Gln Ile Ala Lys Gly Ile Glu Glu Ser Leu Lys
            660                 665                 670

<210> SEQ ID NO 24
<211> LENGTH: 542
<212> TYPE: PRT
<213> ORGANISM: Clostridium difficile

<400> SEQUENCE: 24

Met Gly Leu Asn Leu Lys Asp Tyr Asn Val Thr Gln Glu Cys Ile Ile
1               5                   10                  15

Glu Asp Ile Thr Ser Arg Lys Asp Val Asn Lys Tyr Leu Arg Lys Thr
            20                  25                  30

Ser Ala Pro Ile Thr Glu Leu Thr Gly Ser Asp Arg Tyr Glu Thr Ala
            35                  40                  45

Val Lys Ile Ser Lys Glu Gly Trp Lys Asn Gly Ser Asp Lys Val Val
        50                  55                  60

Ile Ile Asn Gly Asp Val Ser Ile Asp Gly Ile Ile Ser Thr Pro Leu
65              70                  75                  80

Ala Thr Thr Tyr Asn Ala Pro Ile Leu Leu Val Glu Lys Asn Asn Val
                85                  90                  95

Pro Asn Ser Val Lys Ser Glu Leu Lys Arg Leu Asn Pro Arg Asp Val
            100                 105                 110

Ile Ile Ile Gly Asp Glu Asn Ala Ile Ser Lys Thr Thr Ala Asn Gln
        115                 120                 125

Ile Lys Ser Thr Val Asn Ala Ser Gln Thr Arg Leu Lys Gly Ser Asn
130                 135                 140

Arg Tyr Glu Thr Ser Leu Leu Ile Ala Lys Glu Ile Asp Lys Asn His
145                 150                 155                 160

Asp Val Glu Lys Val Tyr Ile Thr Asn Ala Asn Gly Gly Glu Val Asp
            165                 170                 175

Ala Leu Thr Ile Ala Ala Lys Ala Gly Gln Asp Lys Gln Pro Ile Ile
        180                 185                 190

Leu Thr Asp Lys Asn Ser Ile Thr Asp Asn Thr Tyr Lys Trp Leu Lys
            195                 200                 205

Ser Glu Asp Leu Gln Asn Ala Tyr Phe Ile Gly Gly Pro Gln Met Ile
        210                 215                 220
```

```
Ser Thr Asn Val Ile Asn Lys Val Asn Asp Ile Thr Lys Asp Asn Val
225                 230                 235                 240

Thr Asn Asn Arg Val Tyr Gly Ala Asp Arg His Glu Thr Asn Ala Asn
            245                 250                 255

Val Ile Lys Lys Phe Tyr Thr Asp Asp Glu Leu Glu Ala Val Leu Val
        260                 265                 270

Ala Lys Ser Asp Val Leu Val Asp Ala Leu Ala Ala Gly Pro Leu Ala
    275                 280                 285

Ala Asn Leu Lys Ser Pro Ile Leu Ile Thr Pro Lys Thr Tyr Val Ser
290                 295                 300

Ala Tyr His Lys Glu Asn Leu Glu Ala Lys Ser Ala Asn Lys Val Tyr
305                 310                 315                 320

Lys Ile Gly Gly Gly Leu Thr Ser Lys Val Met Asn Ser Ile Ala Ser
                325                 330                 335

Ser Leu Ser Lys His Asn Thr Thr Pro Thr Glu Pro Gly Asn Ser Gly
            340                 345                 350

Gly Lys Thr Val Met Ile Asp Pro Gly His Gly Gly Ser Asp Thr Gly
        355                 360                 365

Thr Thr Gly Lys Pro Leu Gly Gly Ile Lys Glu Lys Asp Tyr Thr Leu
370                 375                 380

Asn Thr Ser Leu Ala Thr Thr Glu Tyr Leu Arg Ser Lys Gly Phe Asn
385                 390                 395                 400

Val Ile Met Thr Arg Asp Thr Asp Lys Thr Leu Ser Leu Gly Asn Arg
                405                 410                 415

Thr Ala Leu Ser Asn Ser Leu Arg Pro Asp Leu Phe Thr Ser Ile His
            420                 425                 430

Tyr Asn Ala Ser Asp Thr Thr Gly Asn Gly Val Glu Val Phe Tyr Lys
        435                 440                 445

Leu Lys Asp Lys Asp Gly Gly Thr Thr Lys Thr Val Ala Thr Asn Ile
    450                 455                 460

Leu Asn Arg Ile Leu Glu Lys Phe Asn Leu Lys Asn Arg Gly Ala Lys
465                 470                 475                 480

Thr Arg Thr Leu Ser Thr Asp Pro Thr Lys Asp Tyr Leu Tyr Val Leu
                485                 490                 495

Arg Asn Asn Asp Met Pro Ala Val Leu Val Glu Cys Ala Phe Leu Asp
            500                 505                 510

Asn Glu Lys Asp Met Ser Leu Leu Asn Thr Ser Asn Lys Val Lys Glu
        515                 520                 525

Met Gly Thr Gln Ile Gly Lys Gly Ile Glu Asp Ser Leu Lys
    530                 535                 540

<210> SEQ ID NO 25
<211> LENGTH: 396
<212> TYPE: PRT
<213> ORGANISM: Clostridium difficile

<400> SEQUENCE: 25

Met Asn Phe Asn Gln Lys Arg Ile Ala Ala Ser Ile Met Ala Thr Ala
1               5                   10                  15

Ile Ile Met Pro Thr Met Gly Asn Leu Ala Tyr Ala Asn Glu Ser Glu
            20                  25                  30

Val Glu Ser Val Ser Ile Glu Ser Arg Thr Ile Thr Gly Asn Ala Val
        35                  40                  45

Asn Phe Arg Lys Gly Pro Gly Thr Asn His Glu Ser Met Gly Lys Leu
```

```
            50                  55                  60
Tyr Lys Gly Asp Lys Val Glu Tyr Val Gly Lys Glu Gly Ser Trp Val
 65                  70                  75                  80

Lys Val Lys Tyr Asn Gly Asn Thr Gly Tyr Val His Gly Asn Tyr Val
                 85                  90                  95

Ala Ile Asn Ser Leu Gly Ser Ser Glu Ser Ser Asp Thr Ser Val
            100                 105                 110

Lys Ser Thr Lys Val Val Thr Ala Lys Gly Leu Asn Phe Arg Thr Gly
            115                 120                 125

Pro Ser Thr Ser Ser Ser Lys Ile Ser Thr Leu Gly Tyr Gly Thr Glu
            130                 135                 140

Val Gly Tyr Ile Ser Glu Ser Asn Gly Trp Ser Lys Ile Ser Ser Asn
145                 150                 155                 160

Gly Arg Val Gly Tyr Val Ser Ser Lys Tyr Leu Gly Thr Ser Val Asn
                165                 170                 175

Asp Ser Thr Asn Glu Asn Ala Glu Asn Ser Ser Asn Asp Leu Val Lys
            180                 185                 190

Gly Thr Lys Val Val Thr Ala Lys Ser Leu Asn Val Arg Thr Gly Pro
            195                 200                 205

Gly Thr Ser His Ser Lys Ile Ala Thr Leu Ser Tyr Gly Thr Glu Val
            210                 215                 220

Gly Ser Ile Ser Glu Ser Gly Gly Trp Thr Lys Val Ser Tyr Gly Asn
225                 230                 235                 240

Gln Thr Gly Tyr Val Ser Ser Gln Tyr Leu Ala Glu Lys Gly Ser Val
                245                 250                 255

Asp Thr Ser Ile Pro Ser Tyr Ser Thr Asn Ser Pro Ser Gln Gly Ala
            260                 265                 270

Asp Ser Val Ile Ser Phe Ala Lys Thr Leu Leu Gly Lys Pro Tyr Val
            275                 280                 285

Trp Gly Ala Glu Gly Pro Asn Ser Phe Asp Cys Ser Gly Phe Thr Gln
            290                 295                 300

Tyr Val Met Lys Lys Ser Val Gly Val Ser Ile Pro Arg Val Ser Arg
305                 310                 315                 320

Asp Gln Ser Lys Tyr Gly Thr Tyr Val Asn Arg Gly Asp Leu Arg Ser
                325                 330                 335

Gly Asp Leu Val Phe Phe Asp Thr Gln Gly Ser Asn Asn Gly Ser Val
            340                 345                 350

Ser His Val Gly Ile Tyr Ile Gly Asn Gly Asp Met Ile His Ala Ser
            355                 360                 365

Ser Gly Ser Ser Lys Lys Val Thr Ile Ser Asn Ile Asn Ser Ser Tyr
            370                 375                 380

Tyr Ser Ser Arg Tyr Val Asn Ala Arg Arg Val Leu
385                 390                 395

<210> SEQ ID NO 26
<211> LENGTH: 235
<212> TYPE: PRT
<213> ORGANISM: Clostridium difficile

<400> SEQUENCE: 26

Met Met Asn Ile Lys Asn Lys Lys His Ile Leu Lys Lys Phe Ile Ala
 1                5                  10                  15

Met Val Leu Ile Ala Gly Val Val Thr Val Glu Ala Gly Ala Ile Thr
                20                  25                  30
```

```
Ala Ser Ala Ala Glu Pro Thr Asn Ser Pro Met Ser Ala Thr Val Asp
        35                  40                  45

Gln Cys Asp Phe Leu Asn Val Arg Ser Gly Ala Ser Ala Asn Asp Ala
 50                      55                  60

Val Val Gly Lys Ile Asn Thr Gly Asp Lys Val Glu Val Leu Glu Leu
 65                  70                  75                  80

His Ser Asn Gly Trp Ile Lys Ile Lys Ser Val Asp Asn Val Thr Gly
                 85                  90                  95

Trp Val Asn Gly Asp Tyr Leu Thr Ile Gln Gly Gly Asn Val Asp Ala
            100                 105                 110

Lys Val Gln Asn Val Leu Asn Leu Ala Phe Lys Gln Gln Gly Lys Pro
        115                 120                 125

Tyr Lys Trp Gly Ala Thr Gly Pro Asn Ser Phe Asp Cys Ser Gly Phe
    130                 135                 140

Thr Ser Tyr Val Tyr Lys Asn Gly Ala Gly Val Asn Leu Pro Arg Val
145                 150                 155                 160

Ser Arg Ser Gln Ala Thr Val Gly Lys Lys Val Ser Arg Ala Glu Leu
                165                 170                 175

Lys Pro Gly Asp Leu Val Phe Phe Gly Ser Gly Ser Ile Asn His
            180                 185                 190

Val Gly Leu Tyr Val Gly Asp Ser Lys Phe Ile His Ser Pro Gln Thr
        195                 200                 205

Gly Asp Val Val Lys Val Thr Ser Met Ala Pro Gly Thr Asn Tyr Ala
    210                 215                 220

Arg Arg Leu Ile Thr Ala Thr Arg Val Leu Gln
225                 230                 235

<210> SEQ ID NO 27
<211> LENGTH: 311
<212> TYPE: PRT
<213> ORGANISM: Clostridium difficile

<400> SEQUENCE: 27

Met Ser Ser Arg Leu Asn Val Arg Ser Gly Ala Gly Thr Asn Tyr Ser
 1               5                  10                  15

Leu Val Gly Lys Ala Asn Asn Gly Asp Val Val Lys Leu Leu Glu Gln
             20                  25                  30

Ser Asn Gly Trp Tyr Lys Ile Lys Leu Ser Asn Gly Val Thr Gly Trp
         35                  40                  45

Ala Ser Ser Gln Tyr Ile Ser Lys Thr Ser Glu Asp Val Gly Thr Asn
 50                  55                  60

Asn Ser Ser Asn Ser Asn Ser Thr Asn Asn Ser Asp Lys Lys Pro Ser
 65                  70                  75                  80

Ser Glu Glu Ser Ile Glu Gly Lys Asn Gly Lys Val Thr Ser Ala Val
                 85                  90                  95

Ser Leu Asn Val Arg Ser Gly Pro Gly Thr Ser Tyr Ser Ile Ile Gly
            100                 105                 110

Lys Leu Asn Gly Gly Asp Val Val Glu Leu Lys Ala Lys Ser Asn Gly
        115                 120                 125

Trp Tyr Lys Val Lys Leu Ser Ser Gly Thr Ile Gly Trp Val Ser Ala
    130                 135                 140

Ser Tyr Ile Ser Glu Thr Asn Glu Asp Thr Lys Glu Lys Pro Asn Ser
145                 150                 155                 160

Ser Ser Asn Gln Asn Ser Gln Ser Asn Ser Asn Ser Lys Pro Ser Phe
                165                 170                 175
```

```
Thr Gly Asn Ser Asp Lys Ser Thr Ala Lys Gly Ser Thr Ile Val Asp
            180                 185                 190

Phe Ala Tyr Thr Leu Ile Gly Ile Pro Tyr Gln Trp Gly Ala Ser Gly
            195                 200                 205

Pro Asp Lys Phe Asp Cys Ser Gly Phe Thr Gln Tyr Val Phe Lys His
            210                 215                 220

Ser Val Gly Val Ser Ile Pro Arg Val Ser Arg Glu Gln Ala Asn Phe
225                 230                 235                 240

Gly Ser Ala Ile Ser Met Gly Asn Tyr Ala Pro Gly Asp Leu Val Tyr
            245                 250                 255

Phe Asp Thr Asp Gly Asp Gly Thr Thr Asn His Val Gly Ile Tyr Val
            260                 265                 270

Gly Asn Ser Lys Phe Ile His Cys Ser Gly Thr Gln Thr Asn Pro Asn
            275                 280                 285

Lys Val Lys Val Asp Asn Leu Thr Ser Ser Tyr Trp Ser Lys Val Leu
            290                 295                 300

Leu Gly Ala Arg Arg Phe Val
305                 310

<210> SEQ ID NO 28
<211> LENGTH: 197
<212> TYPE: PRT
<213> ORGANISM: Clostridium difficile

<400> SEQUENCE: 28

Met Val Leu Glu Asp Asn Gly Asp Trp Leu Lys Val Lys Asp Gly Glu
1               5                   10                  15

Thr Glu Gly Tyr Val Lys Ser Ser Tyr Ile Ser Asp Lys Ala Pro Val
            20                  25                  30

Ile Glu Glu Pro Gln Val Asn Pro Ser Ile Asp Gln Asn Val Asp Ser
            35                  40                  45

Thr Asn Asn Asn Gln Gln Asn Asn Ala Asn Thr Asn Gln Gln Asn Asn
        50                  55                  60

Asn Ser Asn Val Pro Thr Ala Asn Ser Asn Ala Val Gln Ala Val Leu
65                  70                  75                  80

Asn Leu Ala Tyr Ser Lys Gln Gly Cys Pro Tyr Val Trp Gly Ala Glu
            85                  90                  95

Gly Pro Asn Thr Phe Asp Cys Ser Gly Phe Thr Gln Tyr Val Tyr Arg
            100                 105                 110

Asn Ala Val Gly Lys Asn Ile Pro Arg Thr Ser Lys Ala Gln Ser Lys
            115                 120                 125

Tyr Gly Gln Thr Val Ser Lys Ala Asn Leu Gln Pro Gly Asp Leu Val
            130                 135                 140

Phe Phe Thr Thr Asn Gly Ser Gly Ser Val Ser His Val Gly Ile Tyr
145                 150                 155                 160

Val Gly Gly Gly Asn Met Ile His Ser Pro Ser Thr Gly Lys Thr Val
            165                 170                 175

Ser Val Thr Ser Ile Asn Ser Ser Tyr Tyr Thr Ala Arg Phe Val Thr
            180                 185                 190

Ala Lys Arg Ile Leu
            195

<210> SEQ ID NO 29
<211> LENGTH: 376
<212> TYPE: PRT
```

<213> ORGANISM: Clostridium difficile

<400> SEQUENCE: 29

Ala Lys Leu Tyr Lys Gly Lys Thr Val Glu Ile Leu Glu Lys Ser Asn
1               5                   10                  15

Gly Trp Tyr Lys Val Arg Val Ser Ser Val Val Gly Trp Gly Ser
            20                  25                  30

Ala Lys Tyr Ile Ser Thr Ser Gly Ser Glu Gly Thr Ser Ser Gln
        35                  40                  45

Asn Asn Pro Thr Ser Ser Gly Thr Thr Ile Ser Gly Asn Gly Lys Val
    50                  55                  60

Asn Val Ser Ser Arg Leu Asn Val Arg Ser Gly Ala Gly Thr Asn Tyr
65                  70                  75                  80

Ser Leu Val Gly Lys Ala Asn Asn Gly Asp Val Val Lys Leu Leu Glu
                85                  90                  95

Gln Ser Asn Gly Trp Tyr Lys Ile Lys Leu Ser Asn Gly Val Thr Gly
            100                 105                 110

Trp Ala Ser Ser Gln Tyr Ile Ser Lys Thr Ser Glu Asp Val Gly Thr
        115                 120                 125

Asn Asn Ser Ser Asn Ser Asn Ser Thr Asn Asn Ser Asp Lys Lys Pro
    130                 135                 140

Ser Ser Glu Glu Ser Ile Glu Gly Lys Asn Gly Lys Val Thr Ser Ala
145                 150                 155                 160

Val Ser Leu Asn Val Arg Ser Gly Pro Gly Thr Ser Tyr Ser Ile Ile
                165                 170                 175

Gly Lys Leu Asn Gly Gly Asp Val Val Glu Leu Lys Ala Lys Ser Asn
            180                 185                 190

Gly Trp Tyr Lys Val Lys Leu Ser Ser Gly Thr Ile Gly Trp Val Ser
        195                 200                 205

Ala Ser Tyr Ile Ser Glu Thr Asn Glu Asp Thr Lys Glu Lys Pro Asn
    210                 215                 220

Ser Ser Ser Asn Gln Asn Ser Gln Ser Asn Ser Asn Ser Lys Pro Ser
225                 230                 235                 240

Phe Thr Gly Asn Ser Asp Lys Ser Thr Ala Lys Gly Ser Thr Ile Val
                245                 250                 255

Asp Phe Ala Tyr Thr Leu Ile Gly Ile Pro Tyr Gln Trp Gly Ala Ser
            260                 265                 270

Gly Pro Asp Lys Phe Asp Cys Ser Gly Phe Thr Gln Tyr Val Phe Lys
        275                 280                 285

His Ser Val Gly Val Ser Ile Pro Arg Val Ser Arg Glu Gln Ala Asn
    290                 295                 300

Phe Gly Ser Ala Ile Ser Met Gly Asn Tyr Ala Pro Gly Asp Leu Val
305                 310                 315                 320

Tyr Phe Asp Thr Asp Gly Asp Gly Thr Thr Asn His Val Gly Ile Tyr
                325                 330                 335

Val Gly Asn Ser Lys Phe Ile His Cys Ser Gly Thr Gln Thr Asn Pro
            340                 345                 350

Asn Lys Val Lys Val Asp Asn Leu Thr Ser Ser Tyr Trp Ser Lys Val
        355                 360                 365

Leu Leu Gly Ala Arg Arg Phe Val
    370                 375

<210> SEQ ID NO 30
<211> LENGTH: 366

<212> TYPE: PRT
<213> ORGANISM: Clostridium difficile

<400> SEQUENCE: 30

```
Met Lys Lys Ala Ile Ala Ala Leu Gly Ile Gly Ala Val Ala Val Ser
1               5                   10                  15

Val Ser Ser Ile Asn Ala Ser Ala Leu Glu Lys Gly Thr Val Thr Ala
                20                  25                  30

Ser Ala Leu Asn Ile Arg Ser Gly Pro Ser Ser Asp Cys Asp Lys Val
            35                  40                  45

Ala Lys Leu Tyr Lys Gly Lys Thr Val Glu Ile Leu Glu Lys Ser Asn
        50                  55                  60

Gly Trp Tyr Lys Val Arg Val Ser Ser Val Val Gly Trp Gly Ser
65                  70                  75                  80

Ala Lys Tyr Ile Ser Thr Ser Gly Ser Ser Glu Gly Thr Ser Ser Gln
                85                  90                  95

Asn Asn Pro Thr Ser Ser Gly Thr Thr Ile Ser Gly Asn Gly Lys Val
            100                 105                 110

Asn Val Ser Ser Arg Leu Asn Val Arg Ser Gly Ala Gly Thr Asn Tyr
        115                 120                 125

Ser Leu Val Gly Lys Ala Asn Asn Gly Asp Val Val Lys Leu Leu Glu
130                 135                 140

Gln Ser Asn Gly Trp Tyr Lys Ile Lys Leu Ser Asn Gly Val Thr Gly
145                 150                 155                 160

Trp Ala Ser Ser Gln Tyr Ile Ser Lys Thr Ser Glu Asp Val Gly Thr
                165                 170                 175

Asn Asn Ser Ser Asn Ser Asn Ser Thr Asn Asn Ser Asp Lys Lys Pro
            180                 185                 190

Ser Ser Glu Glu Ser Ile Glu Gly Lys Asn Gly Lys Val Thr Ser Ala
        195                 200                 205

Val Ser Leu Asn Val Arg Ser Gly Pro Gly Thr Ser Tyr Ser Ile Ile
210                 215                 220

Gly Lys Leu Asn Gly Gly Asp Val Val Glu Leu Lys Ala Lys Ser Asn
225                 230                 235                 240

Gly Trp Tyr Lys Val Lys Leu Ser Ser Gly Thr Ile Gly Trp Val Ser
                245                 250                 255

Ala Ser Tyr Ile Ser Glu Thr Asn Glu Asp Thr Lys Glu Lys Pro Asn
            260                 265                 270

Ser Ser Ser Asn Gln Asn Ser Gln Ser Asn Ser Asn Ser Lys Pro Ser
        275                 280                 285

Phe Thr Gly Asn Ser Asp Lys Ser Thr Ala Lys Gly Ser Thr Ile Val
290                 295                 300

Asp Phe Ala Tyr Thr Leu Ile Gly Ile Pro Tyr Gln Trp Gly Ala Ser
305                 310                 315                 320

Gly Pro Asp Lys Phe Asp Cys Ser Gly Phe Thr Gln Tyr Val Phe Lys
                325                 330                 335

His Ser Val Gly Val Ser Ile Pro Arg Val Ser Arg Glu Gln Ala Asn
            340                 345                 350

Phe Gly Ser Ala Ile Ser Met Gly Ile Met His Gln Glu Ile
        355                 360                 365
```

<210> SEQ ID NO 31
<211> LENGTH: 285
<212> TYPE: PRT
<213> ORGANISM: Clostridium difficile

<400> SEQUENCE: 31

Met Lys Lys Lys Ile Leu Ile Pro Val Phe Ala Ser Val Met Ala Leu
1               5                   10                  15

Ser Val Ser Ser Ile Val Asn Ala Asp Glu Val Asn Asp Ser Ser Gln
            20                  25                  30

Asn Lys Asp Asp Lys Thr Asn Ala Glu Leu Asn Leu Gly Glu Tyr Lys
        35                  40                  45

Glu Val Lys Tyr Lys Val Ala Lys Ile Lys Asp Gly Val Ala Ile Lys
    50                  55                  60

Ile Arg Glu Glu Gly Gln Val Gln Asn Ile Ala Tyr Ser Gly Asp Glu
65                  70                  75                  80

Phe Thr Val Leu Gly Thr Gln Gly Glu Trp Val Lys Val Lys Val Glu
                85                  90                  95

Asp Gly Glu Gly Trp Leu Ala Thr Arg Tyr Val Asp Ile Ser Glu Gly
            100                 105                 110

Val Gly Tyr Thr Asn Ala Asp Lys Val Asn Leu Arg Lys Asp Lys Ser
        115                 120                 125

Glu Ser Ser Glu Val Ile Glu Glu Leu Glu Lys Gly Ser Ser Leu Leu
    130                 135                 140

Val Leu Glu Asp Asn Gly Asp Trp Leu Lys Val Lys Asp Gly Glu Thr
145                 150                 155                 160

Glu Gly Tyr Val Lys Ser Ser Tyr Ile Ser Asp Lys Ala Pro Val Ile
                165                 170                 175

Glu Glu Pro Gln Val Asn Pro Ser Ile Asp Gln Asn Val Asp Ser Thr
            180                 185                 190

Asn Asn Asn Gln Gln Asn Asn Ala Asn Thr Asn Gln Gln Asn Asn Asn
        195                 200                 205

Ser Asn Val Pro Thr Ala Asn Ser Asn Ala Val Gln Ala Val Leu Asn
    210                 215                 220

Leu Ala Tyr Ser Lys Gln Gly Cys Pro Tyr Val Trp Gly Ala Glu Gly
225                 230                 235                 240

Pro Asn Thr Phe Asp Cys Ser Gly Phe Thr Gln Tyr Val Tyr Arg Asn
                245                 250                 255

Ala Val Gly Lys Asn Ile Pro Arg Thr Ser Lys Ala Gln Ser Lys Tyr
            260                 265                 270

Gly Gln Thr Val Ser Lys Gln Ile Tyr Asn Gln Glu Thr
        275                 280                 285

<210> SEQ ID NO 32
<211> LENGTH: 440
<212> TYPE: PRT
<213> ORGANISM: Clostridium difficile

<400> SEQUENCE: 32

Met Leu Trp Ile Tyr Asp Tyr Lys Asn Leu Leu Gly Gly Val Ile Val
1               5                   10                  15

Val Lys Lys Ala Ile Ala Ala Leu Gly Ile Gly Ala Val Ala Val Ser
            20                  25                  30

Val Ser Ser Ile Asn Ala Ser Ala Leu Glu Lys Gly Thr Val Thr Ala
        35                  40                  45

Ser Ala Leu Asn Ile Arg Ser Gly Pro Ser Ser Asp Cys Asp Lys Val
    50                  55                  60

Ala Lys Leu Tyr Lys Gly Lys Thr Val Glu Ile Leu Glu Lys Ser Asn
65                  70                  75                  80

Gly Trp Tyr Lys Val Arg Val Ser Ser Val Val Gly Trp Gly Ser
                85                  90                  95

Ala Lys Tyr Ile Ser Thr Ser Gly Ser Ser Glu Gly Thr Ser Asn Pro
            100                 105                 110

Asn Asn Ser Thr Ser Ser Gly Thr Thr Ile Ser Gly Asn Gly Lys Val
        115                 120                 125

Asn Val Ser Ser Arg Leu Asn Val Arg Ser Gly Ala Gly Thr Asn Tyr
    130                 135                 140

Ser Leu Val Gly Lys Ala Asn Asn Gly Glu Val Val Lys Leu Leu Glu
145                 150                 155                 160

Gln Ser Asn Gly Trp Tyr Lys Ile Lys Leu Ser Asn Gly Val Thr Gly
                165                 170                 175

Trp Ala Ser Ser Gln Tyr Ile Ser Lys Thr Ser Glu Asp Val Gly Ala
            180                 185                 190

Asn Asn Ser Ser Asn Ser Asn Ser Thr Asn Asn Ser Asp Lys Lys Pro
        195                 200                 205

Ser Ser Glu Glu Ser Ile Glu Gly Lys Asn Gly Lys Val Thr Ser Thr
    210                 215                 220

Val Ser Leu Asn Val Arg Ser Gly Pro Gly Thr Ser Tyr Ser Ile Ile
225                 230                 235                 240

Gly Lys Leu Asn Gly Gly Asp Val Val Glu Leu Lys Ala Lys Asn Asn
                245                 250                 255

Gly Trp Tyr Lys Val Lys Leu Ser Asn Gly Thr Thr Gly Trp Val Ser
            260                 265                 270

Gly Ser Tyr Ile Ser Glu Thr Asn Glu Gly Thr Lys Glu Asn Ser Asn
        275                 280                 285

Ser Ser Ser Asn Gln Asn Ser Gln Ser Asn Asn Ser Lys Pro Ser
    290                 295                 300

Phe Thr Gly Asn Ser Asp Lys Ser Thr Ala Lys Gly Ser Thr Ile Val
305                 310                 315                 320

Asp Phe Ala Tyr Thr Leu Ile Gly Ile Pro Tyr Gln Trp Gly Ala Ser
                325                 330                 335

Gly Pro Asp Lys Phe Asp Cys Ser Gly Phe Thr Gln Tyr Val Phe Lys
            340                 345                 350

His Ser Val Gly Val Ser Ile Pro Arg Val Ser Arg Glu Gln Ala Asn
        355                 360                 365

Phe Gly Ser Ala Ile Ser Met Gly Asn Tyr Ala Pro Gly Asp Leu Val
    370                 375                 380

Tyr Phe Asp Thr Asp Gly Thr Thr Asn His Val Gly Ile Tyr
385                 390                 395                 400

Val Gly Asn Ser Lys Phe Ile His Cys Ser Gly Thr Gln Thr Asn Pro
                405                 410                 415

Asn Lys Val Lys Val Asp Asn Leu Thr Ser Ser Tyr Trp Ser Lys Val
            420                 425                 430

Leu Leu Gly Ala Arg Arg Phe Val
        435                 440

<210> SEQ ID NO 33
<211> LENGTH: 349
<212> TYPE: PRT
<213> ORGANISM: Clostridium difficile

<400> SEQUENCE: 33

Met Lys Lys Lys Ile Leu Ile Pro Val Phe Ala Ser Val Met Ala Leu

```
1               5                   10                  15
Ser Val Ser Ser Ile Val Asn Ala Asp Glu Val Asn Asp Ser Ser Gln
             20                  25                  30
Asn Lys Asp Asp Lys Thr Asn Thr Glu Leu Asn Leu Gly Glu Tyr Lys
             35                  40                  45
Glu Val Lys Tyr Lys Val Ala Lys Ile Lys Asp Val Ala Ile Lys
 50                  55                  60
Ile Arg Glu Glu Gly Gln Val Gln Asn Ile Ala Tyr Ser Gly Asp Glu
 65                  70                  75                  80
Phe Thr Val Leu Gly Thr Gln Gly Glu Trp Val Lys Val Lys Val Glu
                 85                  90                  95
Asp Gly Glu Gly Trp Leu Ala Thr Arg Tyr Val Asp Ile Ser Glu Gly
                100                 105                 110
Val Gly Tyr Thr Asn Ala Asp Lys Val Asn Leu Arg Lys Asp Lys Ser
                115                 120                 125
Glu Ser Ser Glu Val Ile Glu Glu Leu Glu Lys Gly Ser Ser Leu Leu
                130                 135                 140
Val Leu Glu Asp Asn Gly Asp Trp Leu Lys Val Lys Asp Gly Glu Thr
145                 150                 155                 160
Glu Gly Tyr Val Lys Ser Ser Tyr Ile Ser Asp Lys Ala Pro Val Ile
                165                 170                 175
Glu Glu Pro Gln Val Asn Pro Ser Val Asn Gln Asn Gly Asp Ser Thr
                180                 185                 190
Asn Asn Asn Asn Gln Gln Asn Asn Ala Asn Asn Ile Gln Gln Asp Asn
                195                 200                 205
Thr Asn Asp Asn Gln Gln Asn Asn Ser Asn Val Pro Thr Ala Asn
        210                 215                 220
Ser Asn Ala Val Gln Ala Val Leu Asn Leu Ala Tyr Ser Lys Gln Gly
225                 230                 235                 240
Cys Pro Tyr Val Trp Gly Ala Glu Gly Pro Asn Thr Phe Asp Cys Ser
                245                 250                 255
Gly Phe Thr Gln Tyr Val Tyr Arg Asn Ala Val Gly Lys Asn Ile Pro
                260                 265                 270
Arg Thr Ser Lys Ala Gln Ser Lys Tyr Gly Gln Thr Val Ser Lys Ala
                275                 280                 285
Asn Leu Gln Pro Gly Asp Leu Val Phe Phe Thr Thr Asn Gly Ser Gly
                290                 295                 300
Ser Val Ser His Val Gly Ile Tyr Val Gly Gly Asn Met Ile His
305                 310                 315                 320
Ser Pro Ser Thr Gly Lys Thr Val Ser Val Thr Ser Ile Asn Ser Ser
                325                 330                 335
Tyr Tyr Thr Ala Arg Phe Val Thr Ala Lys Arg Ile Leu
                340                 345

<210> SEQ ID NO 34
<211> LENGTH: 383
<212> TYPE: PRT
<213> ORGANISM: Clostridium difficile

<400> SEQUENCE: 34

Met Ser Ile Lys Ile Ile Leu Lys Lys Ile Lys Asn Lys Ile Asn Ile
 1               5                  10                  15
Leu Ile Asp Glu Arg Glu Val Arg Pro Val Ile Leu Asn Asn Arg Ile
                20                  25                  30
```

Leu Met His Lys Lys Leu Phe Thr Thr Leu Phe Leu Ile Met Val
         35                  40                  45

Thr Ser Ser Ser Tyr Val His Ala Asp Asn Ile Lys Lys Ser Asn Phe
 50                  55                  60

Thr Ile Ala Thr Val Lys Asp Gly Leu Cys Leu Asn Ile Arg Asn Ser
65                  70                  75                  80

Lys Asn Glu Ile Ile Ala Lys Ala Asn Ala Gly Glu Leu Lys Val
                 85                  90                  95

Lys Ser Tyr Asn Asn Asp Lys Leu Glu Ile Glu Thr Lys Asp Asn Asn
            100                 105                 110

Lys Gly Tyr Ile Glu Ser Lys Tyr Val Asp Ile Thr Glu Ser Lys Leu
        115                 120                 125

Tyr Val Asn Ala Asp Tyr Met Asn Met Arg Ser Glu Lys Asn Thr Ser
130                 135                 140

Ser Lys Ile Gln Ala Glu Leu Lys Lys Gly Asp Cys Val Ile Val Leu
145                 150                 155                 160

Ser Ser Asp Gly Glu Trp Tyr Lys Val Leu Ser Gly Ser Lys Glu Gly
                165                 170                 175

Tyr Ile Lys Ser Lys Tyr Leu Glu Asp Lys Glu Ser Phe Glu Ser Lys
            180                 185                 190

Thr Ser Asp Asp Val Lys Val Ile Asp Met Gly Asn Ser Asn Ala Lys
        195                 200                 205

Ser Leu Asp Tyr Ile Lys Asp Ile Glu Arg Asn Asn Lys Asn Val Arg
    210                 215                 220

Glu Tyr Ile Lys Arg Leu Asn Asn Lys Gly Ser Asn Tyr Val Val Asp
225                 230                 235                 240

Ser Ile Leu Val Lys Asp Asn Asp Asn Leu Gln Gln Val Pro His Ala
                245                 250                 255

Asp Lys Tyr Ala Ala Gln Lys Leu Leu Asn Leu Ala Tyr Glu Lys Gln
            260                 265                 270

Gly Cys Pro Tyr Val Trp Gly Ala Glu Gly Asp Asn Ser Phe Asp Cys
        275                 280                 285

Ser Gly Phe Thr Met Trp Thr Tyr Lys Asn Ala Leu Gly Ile Asn Ile
290                 295                 300

Pro Arg Val Ser Arg Asp Gln Ala Lys Ile Gly Lys Glu Ile Asp Arg
305                 310                 315                 320

Asn Ser Leu Glu Ala Gly Asp Leu Val Phe Phe Ala Thr Gly Glu Ser
                325                 330                 335

Thr Thr Arg Ile Ser His Val Gly Ile Tyr Val Gly Asn Gly Lys Met
            340                 345                 350

Ile His Ala Pro His Thr Asn Ser Tyr Val Lys Val Gln Asp Ile Thr
        355                 360                 365

Thr Ala Phe Tyr Ser Glu Arg Phe Val Lys Ala Val Arg Leu Leu
    370                 375                 380

<210> SEQ ID NO 35
<211> LENGTH: 953
<212> TYPE: PRT
<213> ORGANISM: Clostridium difficile

<400> SEQUENCE: 35

Met His Gln Val Ser Ser Arg Leu Ser Lys Leu Ala Leu Ser Val Met
1               5                   10                  15

Leu Ala Phe Ala Leu Val Pro Thr Ala Ser Val Ala Ala Met Ala Asp
                20                  25                  30

```
Pro Gln Ile Ser Asp Pro Ala Ser Asp Pro Ile Ile Gln Ser Pro Ser
        35                  40                  45
Ile Asp Gln Gly Val Ser Glu Glu Ala Pro Ala Ser Thr Glu Ser Trp
50                  55                  60
Gln Gly Glu Gly Ser Glu Pro Ala Glu Ala Asp Glu Thr Ala Gln Pro
65                  70                  75                  80
Asp Ser Glu Ala Glu Ala Ser Ala Ala Leu Ala Pro Asp Arg Gln
                85                  90                  95
Pro Val Gly Phe Val Tyr Phe Asp Glu Ser Ser Pro Ser Ala Gly Gly
                100                 105                 110
Ser Gln Leu Val Val Ala Leu Asp Asp Glu Ser Ile Glu Leu Thr
            115                 120                 125
Ser Ala Glu Leu Thr Leu Thr Ala Pro Ser Gly Ala Ser Val Lys Ala
            130                 135                 140
Thr Ala Ser Glu Tyr Ala Gly Asn Ala Ala Leu Phe Ser Val Asp Val
145                 150                 155                 160
Pro Glu Ala Gly Glu Tyr Arg Leu Glu Arg Met Glu Gly Ala Ser Ala
                165                 170                 175
Ala Asp Ser Arg Thr Leu Leu Val Asp Leu Ser Ser Cys Glu Gly Glu
                180                 185                 190
Pro Tyr Ala Phe Met Val Ala Glu Pro Gln Ala Glu Ala Phe Ser Leu
                195                 200                 205
Ser Asp Glu Ser Thr Gly Gly Val Ser Val Tyr Ala Leu Thr Asp Asp
                210                 215                 220
Gly Gln Leu Glu Glu Ala Ser Ser Phe Glu Glu Ala Ala Gln Leu Ser
225                 230                 235                 240
Ala Glu Ala Ala Pro Ala Val Val Gly Arg Ser Ala Ala Ser Gly Ala
                245                 250                 255
Arg Ser Pro Ser Gly Lys Phe Val Val Ala Leu Asp Pro Gly His Gly
                260                 265                 270
Gly Ser Glu Pro Gly Ala Ser Ala Asn Gly Leu Val Glu Arg Glu Leu
            275                 280                 285
Thr Trp Lys Ile Ala Leu Tyr Cys Lys Glu Ala Leu Glu Ser Tyr Ala
            290                 295                 300
Asn Val Glu Val Val Leu Thr Arg Gly Ser Asp Glu Lys Val Ser Leu
305                 310                 315                 320
Val Glu Arg Val Asn Arg Ala Val Asp Ala Gly Ala Asn Val Phe Ile
                325                 330                 335
Ser Leu His Leu Asn Ser Gly Pro Ala Ser Gly Asn Gly Ala Glu Val
                340                 345                 350
Trp Tyr Pro Asn Asp Ser Ser Tyr Arg His Glu Leu His Glu Glu Gly
                355                 360                 365
Ala Gln Leu Ser Ser Lys Ile Leu Glu Lys Leu Thr Ala Leu Gly Leu
            370                 375                 380
Thr Asp Arg Gly Ile Lys Val Arg Asp Ser Glu Arg Val Asp Gly Glu
385                 390                 395                 400
Gly Pro Phe Tyr Tyr Pro Asp Gly Ser Ile Gln Asp Tyr Tyr Thr Val
                405                 410                 415
Ile Glu Ala Ser Arg Glu Ala Gly Ile Val Gly Ile Val Glu His
                420                 425                 430
Ala Phe Leu Ser Asn Lys Ser Asp Ser Asp Lys Leu Lys Ser Glu Ala
            435                 440                 445
```

```
Phe Leu Lys Glu Leu Gly Tyr Ala Asp Ala Glu Gly Ile Ala Glu Thr
    450                 455                 460
Tyr Lys Leu Ser Ser Gly Trp Glu Ile Asp Asn Gly Arg Trp Lys Leu
465                 470                 475                 480
Lys Leu Ala Asp Gly Thr Tyr Ala Thr Ser Ser Trp Gln Gln Val Lys
                485                 490                 495
Gly Lys Lys Tyr Trp Phe Gly Ala Asp Ser Tyr Ala Val Thr Gly Trp
            500                 505                 510
Gln Thr Ile Asp Glu Lys Arg Tyr Tyr Phe Asp Ser Ser Cys Ala Leu
        515                 520                 525
Arg Thr Asp Gly Trp Leu Lys Asp Asp Gly Ser Trp Tyr Trp Leu Ser
530                 535                 540
Ser Ser Gly Val Met Gln Thr Gly Trp Leu Lys Leu Gly Gly Thr Trp
545                 550                 555                 560
Tyr Trp Leu Asp Pro Gln Thr Gly Lys Met Ala Thr Gly Trp Thr Thr
                565                 570                 575
Ala Ser Asp Gly His Arg Tyr Tyr Phe Asp Gly Ser Gly Ala Met Gln
            580                 585                 590
Thr Gly Trp Ala Lys Val Gly Gly Thr Trp Tyr Tyr Leu Ser Gly Ser
        595                 600                 605
Gly Ala Met Gln Thr Gly Trp Leu Ser Lys Gly Gly Ser Trp Tyr Trp
    610                 615                 620
Leu Asp Pro Glu Ser Gly Ala Met Ala Thr Gly Trp Glu Lys Ala Ser
625                 630                 635                 640
Asp Gly Lys Trp Tyr Tyr Phe Glu Gly Ser Gly Ala Met Arg Ser Gly
                645                 650                 655
Gly Trp Met Lys Gln Gly Ser Ser Trp Tyr Tyr Leu Ser Gly Ser Gly
            660                 665                 670
Ala Met Gln Thr Gly Trp Leu Ser Lys Gly Gly Ser Trp Tyr Trp Leu
        675                 680                 685
Asp Pro Glu Ser Gly Arg Met Ala Thr Gly Trp Ala Lys Ala Ala Asp
    690                 695                 700
Gly Lys Trp Tyr Tyr Phe Glu Gly Ser Gly Ala Met Arg Ser Gly Gly
705                 710                 715                 720
Trp Met Lys Gln Gly Gly Thr Trp Tyr Tyr Leu Asn Gly Ser Gly Ala
                725                 730                 735
Met His Thr Gly Trp Leu Asp Leu Asp Gly Lys Arg Tyr Tyr Leu Gly
            740                 745                 750
Glu Ser Gly Ala Met Val Thr Gly Lys Ala Thr Ile Glu Gly Glu Thr
        755                 760                 765
Tyr Arg Phe Asp Ser Ser Gly Ala Leu Leu Pro Ser Asp Ser Ile Met
    770                 775                 780
Gly Pro Ser Leu Ala Thr Val Glu Gln Met Val Thr Leu Phe Asn Ala
785                 790                 795                 800
Gln Gly Val Pro Tyr Pro Val Asp Lys Tyr Ala Ser Arg Gly Ala Ala
                805                 810                 815
Thr Ile Lys Asp Phe Cys Gln Val Leu Leu Asp Gln Ala Arg Ser Glu
            820                 825                 830
Asp Val Arg Ala Glu Val Leu Phe Ala Gln Ala Met Val Glu Thr Gly
        835                 840                 845
Trp Leu Gln Phe Gly Gly Asp Val Asp Arg Asn Gly Lys Val Gln Cys
    850                 855                 860
Asn Phe Gly Gly Leu Gly Ala Thr Gly Asn Gly Val Ala Gly Glu Glu
```

```
865                 870                 875                 880

Phe Pro Asp Val Lys Thr Gly Leu Leu Ala Gln Ala Gln His Leu Lys
                885                 890                 895

Gly Tyr Ala Ser Thr Ala Pro Leu Asn Gln Ser Cys Val Asp Thr Arg
            900                 905                 910

Phe Gly Leu Leu Ala Gly Lys Arg Gly Ser Ala Pro Thr Val Asp Lys
        915                 920                 925

Leu Ser Gly Thr Trp Ala Ala Asp Lys Thr Tyr Gly Thr Lys Val Met
    930                 935                 940

Asn Val Val Asp Lys Leu Leu Gly Tyr
945                 950

<210> SEQ ID NO 36
<211> LENGTH: 317
<212> TYPE: PRT
<213> ORGANISM: Clostridium difficile

<400> SEQUENCE: 36

Met Ala Tyr Thr Asn Ser Lys Leu Ile Ser Tyr Thr Lys Leu Ser Pro
1               5                   10                  15

Asn His Ser Gly Gln Arg Thr His Ser Ile Asp Arg Ile Thr Pro His
            20                  25                  30

Cys Val Val Gly Gln Leu Ser Cys Glu Ser Ile Cys Gly Cys Phe Thr
        35                  40                  45

Ser Pro Ser Arg Gln Ala Ser Cys Asn Tyr Gly Ile Gly Lys Asp Gly
    50                  55                  60

Arg Ile Ser Leu Cys Val Glu Glu Lys Asn Arg Ser Trp Cys Ser Ser
65                  70                  75                  80

Ser Asn Ala Asn Asp Gln Arg Ala Val Thr Ile Glu Cys Ala Ser Asp
                85                  90                  95

Met Ser Glu Pro Tyr Ala Met Asn Ser Ala Val Tyr Asn Ser Leu Val
            100                 105                 110

Arg Leu Cys Thr Asp Ile Cys Lys Arg Asn Gly Lys Lys Lys Leu Leu
        115                 120                 125

Trp Phe Ala Asp Lys Asn Lys Thr Leu Asn Tyr Thr Pro Lys Ala Asp
    130                 135                 140

Glu Met Val Leu Thr Val His Arg Trp Phe Ala Asn Lys Ser Cys Pro
145                 150                 155                 160

Gly Asn Trp Leu Tyr Ser Arg Leu Gly Asp Leu Ala Ala Lys Val Thr
                165                 170                 175

Ser Glu Leu Ser Lys Thr Thr Ser Gly Gly Gly Thr Ala Ser Thr Ser
            180                 185                 190

Gln Met Tyr Arg Val Arg Lys Thr Trp Ser Asp Ser Lys Ser Gln Leu
        195                 200                 205

Gly Ala Tyr Lys Leu Leu Ala Asn Ala Lys Lys Lys Ala Asp Glu Asn
    210                 215                 220

Ala Gly Tyr Lys Val Phe Asp Ala Ser Gly Asn Leu Val Tyr Pro Ala
225                 230                 235                 240

Ala Ala Thr Pro Ala Pro Ala Pro Val Thr Gly Thr Ser Tyr Lys Val
                245                 250                 255

Gln Ile Asp Ile Ala Asn Leu Asn Ile Arg Lys Gly Pro Gly Thr Asn
            260                 265                 270

Tyr Gly Lys Thr Gly Gln Phe Thr Gly Lys Gly Ile Phe Thr Ile Val
        275                 280                 285
```

-continued

Gln Glu Ser Lys Gly Glu Gly Ala Thr Leu Trp Gly Lys Leu Lys Ser
290                 295                 300

Gly Ala Gly Trp Ile Ser Leu Asp Phe Ala Lys Lys Ile
305                 310                 315

<210> SEQ ID NO 37
<211> LENGTH: 353
<212> TYPE: PRT
<213> ORGANISM: Clostridium phage

<400> SEQUENCE: 37

Met Asn His Lys Val His His His His His Met Gln Ser Arg Asn
1               5                   10                  15

Asn Asn Asn Leu Lys Gly Ile Asp Val Ser Asn Trp Lys Gly Asn Ile
            20                  25                  30

Asn Phe Glu Ser Val Lys Asn Asp Gly Val Glu Val Val Tyr Ile Lys
        35                  40                  45

Ala Thr Glu Gly Asn Tyr Phe Lys Asp Lys Tyr Ala Lys Gln Asn Tyr
    50                  55                  60

Glu Gly Ala Lys Glu Gln Gly Leu Ser Val Gly Phe Tyr His Phe Phe
65                  70                  75                  80

Arg Ala Asn Lys Gly Ala Lys Asp Gln Ala Asn Phe Phe Ile Asp Tyr
                85                  90                  95

Leu Asn Glu Ile Gly Ala Val Asn Tyr Asp Cys Lys Leu Ala Leu Asp
            100                 105                 110

Ile Glu Thr Thr Glu Gly Val Gly Val Arg Asp Leu Thr Ser Met Cys
        115                 120                 125

Ile Glu Phe Leu Glu Glu Val Lys Arg Leu Thr Gly Lys Glu Val Val
130                 135                 140

Val Tyr Thr Tyr Thr Ser Phe Ala Asn Asn Leu Asp Ser Arg Leu
145                 150                 155                 160

Gly Asn Tyr Pro Val Trp Ile Ala His Tyr Gly Val Asn Thr Pro Gly
                165                 170                 175

Ala Asn Asn Ile Trp Ser Ser Trp Val Gly Phe Gln Tyr Ser Glu Asn
            180                 185                 190

Gly Ser Val Ala Gly Val Asn Gly Gly Cys Asp Met Asn Glu Phe Thr
        195                 200                 205

Glu Glu Ile Phe Ile Asp Ser Ser Asn Phe Asn Leu Asp Asn Ala Thr
210                 215                 220

Thr Lys Asn Val Ser Thr Lys Leu Asn Ile Arg Ala Lys Gly Thr Thr
225                 230                 235                 240

Asn Ser Lys Ile Ile Gly Ser Ile Pro Ala Gly Glu Thr Phe Lys Ile
                245                 250                 255

Lys Trp Val Asp Glu Asp Tyr Leu Gly Trp Tyr Tyr Val Glu Tyr Asn
            260                 265                 270

Gly Val Val Gly Tyr Val Asn Ala Asp Tyr Val Glu Lys Leu Gln Met
        275                 280                 285

Ala Thr Thr Tyr Asn Val Ser Thr Phe Leu Asn Val Arg Glu Glu Gly
    290                 295                 300

Ser Leu Asn Ser Arg Ile Val Asp Lys Ile Asn Ser Gly Asp Ile Phe
305                 310                 315                 320

Arg Ile Asp Trp Val Asp Ser Asp Phe Ile Gly Trp Tyr Arg Ile Thr
                325                 330                 335

Thr Lys Asn Gly Lys Val Gly Phe Val Asn Ala Glu Phe Val Lys Lys
            340                 345                 350

Leu

<210> SEQ ID NO 38
<211> LENGTH: 227
<212> TYPE: PRT
<213> ORGANISM: Clostridium phage

<400> SEQUENCE: 38

Met Lys Ile Ile Gln Ser Asn Ile His Phe Asn Gly Asn Lys Ala Gly
1               5                   10                  15

Gly Asn Asn Pro Lys Glu Ile Ile Val His Ser Glu His Ser Thr
                20                  25                  30

Ala Asn Val Tyr Asp Ile Asp Arg Trp His Lys Asp Lys Gly Trp Cys
            35                  40                  45

Gly Ile Gly Tyr His Tyr Phe Ile Asp Lys Gln Gly Asn Ile Tyr Thr
    50                  55                  60

Gly Arg Pro Glu Asp Trp Thr Gly Ala His Cys Ile Asp His Asn Thr
65                  70                  75                  80

Lys Ser Ile Gly Ile Cys Leu Gln Gly Arg Leu Gln Thr Glu Lys Val
                85                  90                  95

Thr Asp Pro Gln Tyr Lys Ala Leu Leu Trp Leu Ile Gln Asp Ile Lys
            100                 105                 110

Asn Arg Arg Gly Asn Met Pro Val Tyr Gly His Lys Glu Leu Asn Ser
        115                 120                 125

Thr Asp Cys Pro Gly Asn Leu Asp Leu Asp Lys Leu Arg Arg Asp Leu
    130                 135                 140

Asn Asn Glu Val Val Asp Thr Asn Asp Asp Glu Tyr Arg Glu Asn Ala
145                 150                 155                 160

Thr Val Val Asn Val Ser Ser Tyr Leu Asn Val Arg Ser Lys Pro Ser
                165                 170                 175

Asp Glu Ile Ile Gly Lys Leu Phe Pro Asn Glu Arg Leu Gln Val Asn
            180                 185                 190

Trp Val Asp Ser Asp Tyr Leu Gly Trp Tyr Tyr Val Thr Tyr Arg Val
        195                 200                 205

Asn Gly Thr Asn Lys Leu Lys Asn Gly Tyr Val Ser Ala Lys Tyr Ile
    210                 215                 220

Lys Lys Asp
225

<210> SEQ ID NO 39
<211> LENGTH: 377
<212> TYPE: PRT
<213> ORGANISM: Clostridium phage

<400> SEQUENCE: 39

Met Tyr Ile Asn Gln Ser Asn Ile Lys Phe Asn Gly Leu Arg Tyr Gly
1               5                   10                  15

Asn Asp Pro Asn Lys Ile Ile Ile His Asn Ala Asp Ala Thr Ser Cys
                20                  25                  30

Ser Val Tyr Asp Ile Asp Arg Trp His Lys Gly Asn Gly Trp Ser Gly
            35                  40                  45

Ile Gly Tyr Asp Tyr Phe Ile Arg Lys Glu Gly Ser Val Trp Thr Gly
    50                  55                  60

Arg Pro Glu Asn Ala Ile Gly Ala His Thr Ile Gly Gln Asn Ser Ser
65                  70                  75                  80

Ser Ile Gly Ile Cys Leu Glu Gly Ala Phe Met Arg Glu Lys Pro Thr
            85                  90                  95

Arg Ala Gln Leu Asn Ser Leu Tyr Glu Leu Ile Ala Asp Ile Arg Ala
        100                 105                 110

Arg Arg Gly Asn Leu Pro Val Tyr Gly His Lys Asp Phe Asn Asn Thr
        115                 120                 125

Asp Cys Pro Gly Ile Asn Phe Pro Leu Glu Gln Phe Lys Asn Asn Ser
130                 135                 140

Tyr Arg Pro Thr Gly Gly Glu Ile Val Ser Asp Asn Gly Phe Tyr Arg
145                 150                 155                 160

Ser Asp Glu Glu Arg Thr Asn Ala Thr Ile Val Gly Glu Gly Asn Ile
                165                 170                 175

Glu Val Leu Asp Lys Asn Cys Lys Val Ile Glu Asn Arg Tyr Ile Ser
        180                 185                 190

Ser Leu Asp Arg Val Phe Val Leu Gly Ile Tyr Pro Ala Ser Lys Tyr
        195                 200                 205

Ile Glu Ile Ile Tyr Pro Ala Gly Asn Glu Lys Tyr His Ala Tyr Ile
        210                 215                 220

Ser Ile Glu Asn Tyr Ser Arg Ile Ser Phe Asp Tyr His Met Gln Tyr
225                 230                 235                 240

Lys Asn Asp Asn Gly Val Thr Tyr Val Trp Trp Asp Ser Glu Asp Val
                245                 250                 255

Asn Val Lys Glu His Asn Glu Leu Gln Ala Asn Gln Lys Ala Ser
        260                 265                 270

Pro Met Tyr Arg Val Gly Lys Trp Leu Arg Val Thr Phe Tyr Arg Thr
                275                 280                 285

Asp Gly Thr Pro Ser Asp Gly Phe Val Arg Tyr Glu Gly Glu Gln Ala
290                 295                 300

Val Lys Phe Tyr Glu Glu Lys Ile Lys Glu Gly Ile Val Lys Val
305                 310                 315                 320

Asn Thr Tyr Leu Asn Val Arg Asp Ser Ile Gly Asn Ile Ile Gly
                325                 330                 335

Lys Val Phe Asn Gly Glu Glu Val Ser Ile Ile Trp Thr Lys Asp Gly
                340                 345                 350

Trp Tyr Tyr Ile Asp Tyr Asn Thr Asn His Gly Lys Lys Arg Gly Tyr
                355                 360                 365

Val Ser Ser Lys Tyr Val Glu Val
        370                 375

<210> SEQ ID NO 40
<211> LENGTH: 309
<212> TYPE: PRT
<213> ORGANISM: Clostridium phage

<400> SEQUENCE: 40

Met Ala Val Asn Ile Ile Arg Lys Ile Thr Ser His Gly Ala Gln Gly
1               5                   10                  15

Gly Ala Asn Tyr Pro Thr Trp Ile Val Ile His Glu Thr Asp Asn Glu
            20                  25                  30

Asp Lys Gly Ala Asn Ala Leu Cys His Ala Arg Ala Leu Ala Asn Gly
        35                  40                  45

Asn Leu Ser Cys Ser Ala His Tyr Tyr Val Asp Glu Ser Asn Ile Val
    50                  55                  60

Gln Val His Glu His Trp Thr Val Thr Ser His Val Gly Val Lys Tyr
65                  70                  75                  80

-continued

```
Gly Thr Pro Pro Ile Gly Gly Ile Gly Asn Lys Asn Ser Ile Gly Ile
                85                  90                  95

Glu Ile Cys Val Asn Lys Asp Gly Asn Tyr Ser Gln Ala Arg Gln Asn
            100                 105                 110

Ala Ile Glu Leu Thr Lys Tyr Leu Ile Ser Thr Thr Lys Ile Pro Ala
        115                 120                 125

Ser Arg Val Val Arg His Tyr Asp Ala Cys Lys Lys Tyr Cys Pro Arg
    130                 135                 140

Lys Met Leu Asp Ser Leu Ser Leu Trp Asn Asp Phe Lys Ser Gln Ile
145                 150                 155                 160

Ser Gly Asn Ser Gln Ser Asn Pro Ser Val Asn Ser Ser Ser Gly Leu
                165                 170                 175

Leu Lys Val Gly Ser Arg Glu Asp Lys Val Lys Gln Leu Gln Ala Asn
            180                 185                 190

Leu Asn Lys Leu Gly Tyr Thr Cys Gly Asn Ala Asp Gly Ile Phe Gly
        195                 200                 205

Gln Gly Thr Lys Asn Ala Val Ile Ser Phe Gln Arg Asn Asn Gly Leu
    210                 215                 220

Ser Ala Asp Gly Val Val Gly Glu Ser Thr Trp Asn Lys Ile Leu Ser
225                 230                 235                 240

Asn Leu Glu Val Arg Arg Phe Lys Pro Leu Pro Leu Lys Met Ile Tyr
                245                 250                 255

Asp Ser Pro Ala Ile Gln Ile Arg Asp Gly Phe Val Asn Ile Ser Lys
            260                 265                 270

Tyr Phe Tyr Arg Asp Gln Leu Ile Thr Ala Ile Asp Glu Lys Leu Glu
        275                 280                 285

Phe Tyr Leu Leu Asp Ile Asn Gly Val Lys Ala Trp Ile Pro Lys Lys
    290                 295                 300

Ala Thr Phe Pro Arg
305
```